US012778581B2

(12) United States Patent
Westling et al.

(10) Patent No.: US 12,778,581 B2
(45) Date of Patent: Nov. 3, 2026

(54) MEDICAL IMPLANT DELIVERY SYSTEM AND RELATED METHODS

(71) Applicant: Rotation Medical, Inc., Memphis, TN (US)

(72) Inventors: Thomas A. Westling, Orono, MN (US); Nathaniel Zenz-Olson, Blaine, MN (US)

(73) Assignee: Rotation Medical, Inc.

( * ) Notice: Subject to any disclaimer, the term of this patent is extended or adjusted under 35 U.S.C. 154(b) by 42 days.

(21) Appl. No.: 18/811,232

(22) Filed: Aug. 21, 2024

(65) Prior Publication Data

US 2024/0407781 A1 Dec. 12, 2024

Related U.S. Application Data

(63) Continuation of application No. 17/362,187, filed on Jun. 29, 2021, now Pat. No. 12,096,932, which is a (Continued)

(51) Int. Cl.
*A61B 17/068* (2006.01)
*A61B 17/00* (2006.01)
(Continued)

(52) U.S. Cl.
CPC .... *A61B 17/0682* (2013.01); *A61B 17/00234* (2013.01); *A61B 17/064* (2013.01); (Continued)

(58) Field of Classification Search
CPC ... A61B 17/00; A61B 17/064; A61B 17/0682; A61B 17/00234; A61B 17/10; (Continued)

(56) References Cited

U.S. PATENT DOCUMENTS 511,238 A 12/1893 Hieatzman et al.
765,793 A 7/1904 Ruckel
(Continued)

FOREIGN PATENT DOCUMENTS

AU 2010256474 B2 12/2010
CA 2390508 A1 5/2001
(Continued)

OTHER PUBLICATIONS

"Rotator Cuff Tear," Wikipedia, the free encyclopedia, 14 pages, Downloaded on Dec. 6, 2012.
(Continued)

*Primary Examiner* — Vi X Nguyen
(74) *Attorney, Agent, or Firm* — Seager, Tufte & Wickhem LLP

(57) ABSTRACT

A fastener delivery tool configured to deliver a fastener into tissue of a patient including a shaft, a handle assembly connected to a proximal end of the shaft, one or more prongs connected to a distal end of the shaft, and a fastener push rod received at least partially within the shaft, wherein the fastener push rod is connected to the handle assembly, wherein the fastener push rod is moveable relative to the shaft, and wherein the fastener push rod includes one or more detents configured to be received within a passageway of a fastener and secure the fastener to the fastener push rod with friction.

11 Claims, 17 Drawing Sheets

Related U.S. Application Data continuation of application No. 16/170,603, filed on Oct. 25, 2018, now Pat. No. 11,076,851, which is a continuation of application No. 14/931,567, filed on Nov. 3, 2015, now Pat. No. 10,123,796.

(60) Provisional application No. 62/075,026, filed on Nov. 4, 2014.

(51) Int. Cl.
*A61B 17/064* (2006.01)
*A61B 17/10* (2006.01)
*A61B 90/00* (2016.01)
*A61F 2/08* (2006.01)

(52) U.S. Cl.
CPC .......... *A61B 17/0642* (2013.01); *A61B 17/10* (2013.01); *A61B 2017/0053* (2013.01); *A61B 2017/0688* (2013.01); *A61B 90/03* (2016.02); *A61B 90/361* (2016.02); *A61B 2217/005* (2013.01); *A61B 2217/007* (2013.01); *A61F 2/0805* (2013.01)

(58) Field of Classification Search
CPC ..... A61B 17/0642; A61B 90/00; A61B 90/03; A61B 90/361; A61F 2/0805
See application file for complete search history.

(56) References Cited

U.S. PATENT DOCUMENTS 1,728,316 A 9/1929 Von Wachenfeldt
1,855,546 A 4/1932 File
1,868,100 A 7/1932 Goodstein
1,910,688 A 5/1933 Goodstein
1,940,351 A 12/1933 Howard
2,034,785 A 3/1936 Wappler
2,075,508 A 3/1937 Davidson
2,131,321 A 9/1938 Hart
2,154,688 A 4/1939 Matthews et al.
2,158,242 A 5/1939 Maynard
2,199,025 A 4/1940 Conn
2,201,610 A 5/1940 Dawson, Jr.
2,254,620 A 9/1941 Miller
2,277,931 A 3/1942 Moe
2,283,814 A 5/1942 La Place
2,316,297 A 4/1943 Southerland et al.
2,390,508 A 12/1945 Carleton
2,397,240 A 3/1946 Butler
2,421,193 A 5/1947 Gardner
2,571,813 A 10/1951 Austin
2,630,316 A 3/1953 Foster
2,684,070 A 7/1954 Kelsey
2,744,251 A 5/1956 Vollmer
2,790,341 A 4/1957 Keep et al.
2,817,339 A 12/1957 Sullivan
2,825,162 A 3/1958 Flood
2,881,762 A 4/1959 Lowrie
2,910,067 A 10/1959 White
3,068,870 A 12/1962 Levin
3,077,812 A 2/1963 Dietrich
3,103,666 A 9/1963 Bone
3,120,377 A 2/1964 Lipschultz et al.
3,123,077 A 3/1964 Alcamo
3,209,754 A 10/1965 Brown
3,221,746 A 12/1965 Noble
3,470,834 A 10/1969 Bone
3,527,223 A 9/1970 Shein
3,570,497 A 3/1971 Lemole
3,577,837 A 5/1971 Bader, Jr.
3,579,831 A 5/1971 Stevens et al.
3,643,851 A 2/1972 Green et al.
3,687,138 A 8/1972 Jarvik
3,716,058 A 2/1973 Tanner, Jr.
3,717,294 A 2/1973 Green
3,740,994 A 6/1973 DeCarlo, Jr.
3,757,629 A 9/1973 Schneider
3,777,538 A 12/1973 Weatherly et al.
3,837,555 A 9/1974 Green
3,845,772 A 11/1974 Smith
3,875,648 A 4/1975 Bone
3,960,147 A 6/1976 Murray
3,976,079 A 8/1976 Samuels et al.
4,014,492 A 3/1977 Rothfuss
4,127,227 A 11/1978 Green
4,259,959 A 4/1981 Walker
4,263,903 A 4/1981 Griggs
4,265,226 A 5/1981 Cassimally
4,317,451 A 3/1982 Cerwin et al.
4,400,833 A 8/1983 Kurland
4,422,567 A 12/1983 Haynes
4,454,875 A 6/1984 Pratt et al.
4,480,641 A 11/1984 Failla et al.
4,485,816 A 12/1984 Krumme
4,526,174 A 7/1985 Froehlich
4,549,545 A 10/1985 Levy
4,570,623 A 2/1986 Ellison et al.
4,586,197 A 5/1986 Hubbard
4,595,007 A 6/1986 Mericle
4,610,251 A 9/1986 Kumar
4,624,254 A 11/1986 McGarry et al.
4,627,437 A 12/1986 Bedi et al.
4,632,100 A 12/1986 Somers et al.
4,635,634 A 1/1987 Santos
4,635,637 A 1/1987 Schreiber
4,669,473 A 6/1987 Richards et al.
4,696,300 A 9/1987 Anderson
4,719,917 A 1/1988 Barrows et al.
4,738,255 A 4/1988 Goble et al.
4,741,330 A 5/1988 Hayhurst
4,762,260 A 8/1988 Richards et al.
4,799,495 A 1/1989 Hawkins et al.
4,809,695 A 3/1989 Gwathmey et al.
4,851,005 A 7/1989 Hunt et al.
4,858,608 A 8/1989 McQuilkin
4,884,572 A 12/1989 Bays et al.
4,887,601 A 12/1989 Richards
4,924,866 A 5/1990 Yoon
4,930,674 A 6/1990 Barak
4,968,315 A 11/1990 Gatturna
4,976,715 A 12/1990 Bays et al.
4,994,073 A 2/1991 Green
4,997,436 A 3/1991 Oberlander
5,002,563 A 3/1991 Pyka et al.
5,013,316 A 5/1991 Goble et al.
5,015,249 A 5/1991 Nakao et al.
5,037,422 A 8/1991 Hayhurst et al.
5,041,129 A 8/1991 Hayhurst et al.
5,046,513 A 9/1991 Gatturna et al.
5,053,047 A 10/1991 Yoon
5,059,206 A 10/1991 Winters
5,062,563 A 11/1991 Green et al.
5,100,417 A 3/1992 Cerier et al.
5,102,421 A 4/1992 Anspach, Jr.
5,116,357 A 5/1992 Eberbach
5,122,155 A 6/1992 Eberbach
5,123,913 A 6/1992 Wilk et al.
RE34,021 E 8/1992 Mueller et al.
5,141,515 A 8/1992 Eberbach
5,141,520 A 8/1992 Goble et al.
5,156,609 A 10/1992 Nakao et al.
5,156,616 A 10/1992 Meadows et al.
5,167,665 A 12/1992 Mckinney
5,171,259 A 12/1992 Inoue
5,174,295 A 12/1992 Christian et al.
5,174,487 A 12/1992 Rothfuss et al.
5,176,682 A 1/1993 Chow
5,176,692 A 1/1993 Wilk et al.
5,203,787 A 4/1993 Noblitt et al.
5,217,472 A 6/1993 Green et al.
5,224,946 A 7/1993 Hayhurst et al.
5,242,457 A 9/1993 Akopov et al.
5,246,441 A 9/1993 Ross et al.

(56) References Cited

U.S. PATENT DOCUMENTS 5,251,642 A 10/1993 Handlos
5,261,914 A 11/1993 Warren
5,269,753 A 12/1993 Wilk
5,269,783 A 12/1993 Sander
5,282,829 A 2/1994 Hermes
5,289,963 A 3/1994 McGarry et al.
5,290,217 A 3/1994 Campos
5,304,187 A 4/1994 Green et al.
5,333,624 A 8/1994 Tovey
5,342,396 A 8/1994 Cook
5,350,400 A 9/1994 Esposito et al.
5,352,229 A 10/1994 Goble et al.
5,354,292 A 10/1994 Braeuer et al.
5,364,408 A 11/1994 Gordon
5,366,460 A 11/1994 Eberbach
5,370,650 A 12/1994 Tovey et al.
5,372,604 A 12/1994 Trott
5,380,334 A 1/1995 Torrie et al.
5,383,477 A 1/1995 DeMatteis
5,397,332 A 3/1995 Kammerer et al.
5,403,326 A 4/1995 Harrison et al.
5,405,360 A 4/1995 Tovey
5,411,522 A 5/1995 Trott
5,411,523 A 5/1995 Goble
5,417,691 A 5/1995 Hayhurst
5,417,712 A 5/1995 Whittaker et al.
5,425,490 A 6/1995 Goble et al.
5,439,468 A 8/1995 Schulze et al.
5,441,502 A 8/1995 Bartlett
5,441,508 A 8/1995 Gazielly et al.
5,447,513 A 9/1995 Davison et al.
5,456,720 A 10/1995 Schultz et al.
5,458,579 A 10/1995 Chodorow et al.
5,464,403 A 11/1995 Kieturakis et al.
5,478,354 A 12/1995 Tovey et al.
5,486,197 A 1/1996 Le et al.
5,497,933 A 3/1996 DeFonzo et al.
5,500,000 A 3/1996 Feagin et al.
5,501,695 A 3/1996 Anspach, Jr. et al.
5,503,623 A 4/1996 Tilton, Jr.
5,505,735 A 4/1996 Li
5,507,754 A 4/1996 Green et al.
5,520,185 A 5/1996 Soni et al.
5,520,700 A 5/1996 Beyar et al.
5,522,817 A 6/1996 Sander et al.
5,538,297 A 7/1996 Mc Naughton et al.
5,545,180 A 8/1996 Le et al.
5,548,893 A 8/1996 Koelfgen et al.
5,560,532 A 10/1996 DeFonzo et al.
5,562,689 A 10/1996 Green et al.
5,569,306 A 10/1996 Thal
5,582,616 A 12/1996 Bolduc et al.
5,584,835 A 12/1996 Greenfield
5,593,421 A 1/1997 Bauer
5,601,573 A 2/1997 Fogelberg et al.
5,618,314 A 4/1997 Harwin et al.
5,622,257 A 4/1997 Deschenes et al.
5,628,751 A 5/1997 Sander et al.
5,643,319 A 7/1997 Green et al.
5,643,321 A 7/1997 McDevitt
5,647,874 A 7/1997 Hayhurst
5,649,963 A 7/1997 McDevitt
5,662,683 A 9/1997 Kay
5,667,513 A 9/1997 Torrie et al.
5,674,245 A 10/1997 Ilgen
5,681,342 A 10/1997 Benchetrit
5,702,215 A 12/1997 Li
5,713,903 A 2/1998 Sander et al.
5,720,753 A 2/1998 Sander et al.
5,725,541 A 3/1998 Anspach, III et al.
5,741,282 A 4/1998 Anspach, III et al.
5,766,246 A 6/1998 Mulhauser et al.
5,782,864 A 7/1998 Lizardi
5,797,909 A 8/1998 Michelson
5,797,931 A 8/1998 Bito et al.
5,797,963 A 8/1998 McDevitt
5,807,403 A 9/1998 Beyar et al.
5,830,221 A 11/1998 Stein et al.
5,833,700 A 11/1998 Fogelberg et al.
5,836,961 A 11/1998 Kieturakis et al.
5,868,762 A 2/1999 Cragg et al.
5,873,891 A 2/1999 Sohn
5,885,258 A 3/1999 Sachdeva et al.
5,885,294 A 3/1999 Pedlick et al.
5,893,856 A 4/1999 Jacob et al.
5,904,696 A 5/1999 Rosenman
5,919,184 A 7/1999 Tilton, Jr.
5,922,026 A 7/1999 Chin
5,928,244 A 7/1999 Tovey et al.
5,948,000 A 9/1999 Larsen et al.
5,957,939 A 9/1999 Heaven et al.
5,957,953 A 9/1999 Dipoto et al.
5,968,044 A 10/1999 Nicholson et al.
5,980,557 A 11/1999 Iserin et al.
5,989,265 A 11/1999 Bouquet De La Joliniere et al.
5,997,552 A 12/1999 Person et al.
6,063,088 A 5/2000 Winslow
6,156,045 A 12/2000 Ulbrich et al.
6,179,840 B1 1/2001 Bowman
6,193,731 B1 2/2001 Oppelt et al.
6,193,733 B1 2/2001 Adams
6,245,072 B1 6/2001 Zdeblick et al.
6,302,885 B1 10/2001 Essiger
6,312,442 B1 11/2001 Kieturakis et al.
6,315,789 B1 11/2001 Cragg
6,318,616 B1 11/2001 Pasqualucci et al.
6,322,563 B1 11/2001 Cummings et al.
6,325,805 B1 12/2001 Ogilvie et al.
6,342,057 B1 1/2002 Brace et al.
6,387,113 B1 5/2002 Hawkins et al.
6,391,333 B1 5/2002 Li et al.
6,413,274 B1 7/2002 Pedros
6,425,900 B1 7/2002 Knodel et al.
6,436,110 B2 8/2002 Bowman et al.
6,447,522 B2 9/2002 Gambale et al.
6,447,524 B1 9/2002 Knodel et al.
6,478,803 B1 11/2002 Kapec et al.
6,482,178 B1 11/2002 Andrews et al.
6,482,210 B1 11/2002 Skiba et al.
6,506,190 B1 1/2003 Walshe
6,511,499 B2 1/2003 Schmieding et al.
6,517,564 B1 2/2003 Grafton et al.
6,524,316 B1 2/2003 Nicholson et al.
6,527,795 B1 3/2003 Lizardi
6,530,933 B1 3/2003 Yeung et al.
6,540,769 B1 4/2003 Miller, III
6,551,333 B2 4/2003 Kuhns et al.
6,554,852 B1 4/2003 Oberlander
6,569,186 B1 5/2003 Winters et al.
6,575,976 B2 6/2003 Grafton
6,599,286 B2 7/2003 Campin et al.
6,599,289 B1 7/2003 Bojarski et al.
6,620,185 B1 9/2003 Harvie et al.
6,626,930 B1 9/2003 Allen et al.
6,629,988 B2 10/2003 Weadock
6,638,297 B1 10/2003 Huitema
6,648,893 B2 11/2003 Dudasik
6,666,872 B2 12/2003 Barreiro et al.
6,673,094 B1 1/2004 McDevitt et al.
6,685,728 B2 2/2004 Sinnott et al.
6,692,506 B1 2/2004 Ory et al.
6,723,099 B1 4/2004 Goshert
6,726,704 B1 4/2004 Loshakove et al.
6,726,705 B2 4/2004 Peterson et al.
6,740,100 B2 5/2004 Demopulos et al.
6,746,472 B2 6/2004 Frazier et al.
6,764,500 B1 7/2004 Muijs Van De Moer et al.
6,770,073 B2 8/2004 McDevitt et al.
6,779,701 B2 8/2004 Bailly et al.
6,800,081 B2 10/2004 Parodi
6,835,206 B2 12/2004 Jackson
6,849,078 B2 2/2005 Durgin et al.
6,887,259 B2 5/2005 Lizardi
6,926,723 B1 8/2005 Mulhauser et al.

(56) References Cited

U.S. PATENT DOCUMENTS

| | | | |
|---|---|---|---|
| 6,932,834 | B2 | 8/2005 | Lizardi et al. |
| 6,939,365 | B1 | 9/2005 | Fogarty et al. |
| 6,946,003 | B1 | 9/2005 | Wolowacz et al. |
| 6,949,117 | B2 | 9/2005 | Gambale et al. |
| 6,964,685 | B2 | 11/2005 | Murray et al. |
| 6,966,916 | B2 | 11/2005 | Kumar |
| 6,972,027 | B2 | 12/2005 | Fallin et al. |
| 6,984,241 | B2 | 1/2006 | Lubbers et al. |
| 6,991,597 | B2 | 1/2006 | Gellman et al. |
| 7,008,435 | B2 | 3/2006 | Cummins |
| 7,021,316 | B2 | 4/2006 | Leiboff |
| 7,025,772 | B2 | 4/2006 | Gellman et al. |
| 7,033,379 | B2 | 4/2006 | Peterson |
| 7,037,324 | B2 | 5/2006 | Martinek |
| 7,048,171 | B2 | 5/2006 | Thornton et al. |
| 7,063,711 | B1 | 6/2006 | Loshakove et al. |
| 7,083,638 | B2 | 8/2006 | Foerster |
| 7,087,064 | B1 | 8/2006 | Hyde |
| 7,112,214 | B2 | 9/2006 | Peterson et al. |
| 7,118,581 | B2 | 10/2006 | Friden |
| 7,144,413 | B2 | 12/2006 | Wilford et al. |
| 7,144,414 | B2 | 12/2006 | Harvie et al. |
| 7,150,750 | B2 | 12/2006 | Damarati |
| 7,153,314 | B2 | 12/2006 | Laufer et al. |
| 7,160,314 | B2 | 1/2007 | Sgro et al. |
| 7,160,326 | B2 | 1/2007 | Ball |
| 7,163,551 | B2 | 1/2007 | Anthony et al. |
| 7,163,563 | B2 | 1/2007 | Schwartz et al. |
| 7,169,157 | B2 | 1/2007 | Kayan |
| 7,189,251 | B2 | 3/2007 | Kay |
| 7,201,754 | B2 | 4/2007 | Stewart et al. |
| 7,214,232 | B2 | 5/2007 | Bowman et al. |
| 7,226,469 | B2 | 6/2007 | Benavitz et al. |
| 7,229,452 | B2 | 6/2007 | Kayan |
| 7,247,164 | B1 | 7/2007 | Ritchart et al. |
| 7,303,577 | B1 | 12/2007 | Dean |
| 7,309,337 | B2 | 12/2007 | Colleran et al. |
| 7,320,692 | B1 | 1/2008 | Bender et al. |
| 7,320,701 | B2 | 1/2008 | Haut et al. |
| 7,322,935 | B2 | 1/2008 | Palmer et al. |
| 7,326,231 | B2 | 2/2008 | Phillips et al. |
| 7,343,920 | B2 | 3/2008 | Toby et al. |
| 7,368,124 | B2 | 5/2008 | Chun et al. |
| 7,377,934 | B2 | 5/2008 | Lin et al. |
| 7,381,213 | B2 | 6/2008 | Lizardi |
| 7,390,329 | B2 | 6/2008 | Westra et al. |
| 7,399,304 | B2 | 7/2008 | Gambale et al. |
| 7,404,824 | B1 | 7/2008 | Webler et al. |
| 7,416,554 | B2 | 8/2008 | Lam et al. |
| 7,452,368 | B2 | 11/2008 | Liberatore et al. |
| 7,460,913 | B2 | 12/2008 | Kuzma et al. |
| 7,463,933 | B2 | 12/2008 | Wahlstrom et al. |
| 7,465,308 | B2 | 12/2008 | Sikora et al. |
| 7,481,832 | B1 | 1/2009 | Meridew et al. |
| 7,485,124 | B2 | 2/2009 | Kuhns et al. |
| 7,497,854 | B2 | 3/2009 | Gill et al. |
| 7,500,972 | B2 | 3/2009 | Voegele et al. |
| 7,500,980 | B2 | 3/2009 | Gill et al. |
| 7,500,983 | B1 | 3/2009 | Kaiser et al. |
| 7,503,474 | B2 | 3/2009 | Hillstead et al. |
| 7,506,791 | B2 | 3/2009 | Omaits et al. |
| 7,559,941 | B2 | 7/2009 | Zannis et al. |
| 7,572,276 | B2 | 8/2009 | Lim et al. |
| 7,585,311 | B2 | 9/2009 | Green et al. |
| 7,766,208 | B2 | 8/2010 | Epperly et al. |
| 7,771,440 | B2 | 8/2010 | Ortiz et al. |
| 7,776,057 | B2 | 8/2010 | Laufer et al. |
| 7,780,685 | B2 | 8/2010 | Hunt et al. |
| 7,785,255 | B2 | 8/2010 | Malkani |
| 7,807,192 | B2 | 10/2010 | Li et al. |
| 7,819,880 | B2 | 10/2010 | Zannis et al. |
| 7,819,888 | B2 | 10/2010 | Johanson et al. |
| 7,918,879 | B2 | 4/2011 | Yeung et al. |
| 7,931,660 | B2 | 4/2011 | Aranyi et al. |
| 8,034,076 | B2 | 10/2011 | Criscuolo et al. |
| 8,114,101 | B2 | 2/2012 | Criscuolo et al. |
| 8,197,837 | B2 | 6/2012 | Jamiolkowski et al. |
| 8,668,718 | B2 | 3/2014 | Euteneuer et al. |
| 8,763,878 | B2 | 7/2014 | Euteneuer et al. |
| 8,821,536 | B2 | 9/2014 | Euteneuer et al. |
| 8,821,537 | B2 | 9/2014 | Euteneuer et al. |
| 8,864,780 | B2 | 10/2014 | Euteneuer et al. |
| 8,894,669 | B2 | 11/2014 | Nering et al. |
| 9,033,201 | B2 | 5/2015 | Euteneuer |
| 9,095,337 | B2 | 8/2015 | Euteneuer et al. |
| 9,101,460 | B2 | 8/2015 | Euteneuer et al. |
| 9,107,661 | B2 | 8/2015 | Euteneuer et al. |
| 9,113,977 | B2 | 8/2015 | Euteneuer et al. |
| 9,125,650 | B2 | 9/2015 | Euteneuer et al. |
| 9,179,961 | B2 | 11/2015 | Euteneuer et al. |
| 9,192,013 | B1 | 11/2015 | van de Ven et al. |
| 9,198,751 | B2 | 12/2015 | Euteneuer et al. |
| 9,204,940 | B2 | 12/2015 | Euteneuer et al. |
| 9,247,978 | B2 | 2/2016 | Euteneuer et al. |
| 9,271,726 | B2 | 3/2016 | Euteneuer |
| 9,314,314 | B2 | 4/2016 | Euteneuer et al. |
| 9,314,331 | B2 | 4/2016 | Euteneuer et al. |
| 9,370,356 | B2 | 6/2016 | Euteneuer et al. |
| 9,393,103 | B2 | 7/2016 | Van Kampen et al. |
| 10,123,796 | B2 | 11/2018 | Westling et al. |
| 2002/0077687 | A1 | 6/2002 | Ahn |
| 2002/0090725 | A1 | 7/2002 | Simpson et al. |
| 2002/0123767 | A1 | 9/2002 | Prestel |
| 2002/0165559 | A1 | 11/2002 | Grant et al. |
| 2002/0169465 | A1 | 11/2002 | Bowman et al. |
| 2003/0073979 | A1 | 4/2003 | Naimark et al. |
| 2003/0125748 | A1 | 7/2003 | Li et al. |
| 2003/0135224 | A1 | 7/2003 | Blake, III |
| 2003/0212456 | A1 | 11/2003 | Lipchitz et al. |
| 2004/0059416 | A1 | 3/2004 | Murray et al. |
| 2004/0092937 | A1 | 5/2004 | Criscuolo et al. |
| 2004/0138705 | A1 | 7/2004 | Heino et al. |
| 2004/0167519 | A1 | 8/2004 | Weiner et al. |
| 2004/0220574 | A1 | 11/2004 | Pelo et al. |
| 2005/0015021 | A1 | 1/2005 | Shiber |
| 2005/0049618 | A1 | 3/2005 | Masuda et al. |
| 2005/0051597 | A1 | 3/2005 | Toledano |
| 2005/0059996 | A1 | 3/2005 | Bauman et al. |
| 2005/0060033 | A1 | 3/2005 | Vacanti et al. |
| 2005/0107807 | A1 * | 5/2005 | Nakao ................ A61B 17/1285 606/139 |
| 2005/0113736 | A1 | 5/2005 | Orr et al. |
| 2005/0171569 | A1 | 8/2005 | Girard et al. |
| 2005/0187576 | A1 | 8/2005 | Whitman et al. |
| 2005/0240222 | A1 | 10/2005 | Shipp |
| 2005/0274768 | A1 | 12/2005 | Cummins et al. |
| 2006/0074423 | A1 | 4/2006 | Alleyne et al. |
| 2006/0178743 | A1 | 8/2006 | Carter |
| 2006/0235442 | A1 | 10/2006 | Huitema |
| 2006/0293760 | A1 | 12/2006 | DeDeyne |
| 2007/0078477 | A1 | 4/2007 | Heneveld, Sr. et al. |
| 2007/0083236 | A1 | 4/2007 | Sikora et al. |
| 2007/0112361 | A1 | 5/2007 | Schonholz et al. |
| 2007/0179531 | A1 | 8/2007 | Thornes |
| 2007/0185506 | A1 | 8/2007 | Jackson |
| 2007/0190108 | A1 | 8/2007 | Datta et al. |
| 2007/0219558 | A1 | 9/2007 | Deutsch |
| 2007/0270804 | A1 | 11/2007 | Chudik |
| 2007/0288023 | A1 | 12/2007 | Pellegrino et al. |
| 2008/0027470 | A1 | 1/2008 | Hart et al. |
| 2008/0051888 | A1 | 2/2008 | Ratcliffe et al. |
| 2008/0065153 | A1 | 3/2008 | Allard et al. |
| 2008/0090936 | A1 | 4/2008 | Fujimura et al. |
| 2008/0125869 | A1 | 5/2008 | Paz et al. |
| 2008/0135600 | A1 | 6/2008 | Hiranuma et al. |
| 2008/0139473 | A1 | 6/2008 | Ladner et al. |
| 2008/0173691 | A1 | 7/2008 | Mas et al. |
| 2008/0188874 | A1 | 8/2008 | Henderson |
| 2008/0188936 | A1 | 8/2008 | Ball et al. |
| 2008/0195119 | A1 | 8/2008 | Ferree |
| 2008/0200949 | A1 | 8/2008 | Hiles et al. |
| 2008/0241213 | A1 | 10/2008 | Chun et al. |
| 2008/0272173 | A1 | 11/2008 | Coleman et al. |
| 2008/0306408 | A1 | 12/2008 | Lo |

(56) References Cited

U.S. PATENT DOCUMENTS

| | | | |
|---|---|---|---|
| 2008/0312688 A1 | 12/2008 | Nawrocki et al. | |
| 2009/0001122 A1 | 1/2009 | Prommersberger et al. | |
| 2009/0012521 A1 | 1/2009 | Axelson, Jr. et al. | |
| 2009/0030434 A1 | 1/2009 | Paz et al. | |
| 2009/0069806 A1 | 3/2009 | De La Mora Levy et al. | |
| 2009/0076541 A1 | 3/2009 | Chin et al. | |
| 2009/0105535 A1 | 4/2009 | Green et al. | |
| 2009/0112085 A1 | 4/2009 | Eby | |
| 2009/0134198 A1 | 5/2009 | Knodel et al. | |
| 2009/0156986 A1 | 6/2009 | Trenhaile | |
| 2009/0156997 A1 | 6/2009 | Trenhaile | |
| 2009/0182245 A1 | 7/2009 | Zambelli | |
| 2009/0242609 A1 | 10/2009 | Kanner | |
| 2010/0145367 A1 | 6/2010 | Ratcliffe | |
| 2010/0147922 A1 | 6/2010 | Olson | |
| 2010/0163598 A1 | 7/2010 | Belzer | |
| 2010/0191332 A1 | 7/2010 | Euteneuer et al. | |
| 2010/0211097 A1 | 8/2010 | Hadba et al. | |
| 2010/0241227 A1 | 9/2010 | Euteneuer et al. | |
| 2010/0249801 A1 | 9/2010 | Sengun et al. | |
| 2010/0256675 A1 | 10/2010 | Romans | |
| 2010/0274278 A1 | 10/2010 | Fleenor et al. | |
| 2010/0292715 A1 | 11/2010 | Nering et al. | |
| 2010/0292791 A1 | 11/2010 | Lu et al. | |
| 2010/0312250 A1 | 12/2010 | Euteneuer et al. | |
| 2010/0312275 A1 | 12/2010 | Euteneuer et al. | |
| 2010/0327042 A1 | 12/2010 | Amid et al. | |
| 2011/0000950 A1 | 1/2011 | Euteneuer et al. | |
| 2011/0004221 A1 | 1/2011 | Euteneuer et al. | |
| 2011/0011917 A1 | 1/2011 | Loulmet | |
| 2011/0034942 A1 | 2/2011 | Levin et al. | |
| 2011/0040310 A1 | 2/2011 | Levin et al. | |
| 2011/0040311 A1 | 2/2011 | Levin et al. | |
| 2011/0066166 A1 | 3/2011 | Levin et al. | |
| 2011/0079627 A1 | 4/2011 | Cardinale et al. | |
| 2011/0106154 A1 | 5/2011 | DiMatteo et al. | |
| 2011/0114700 A1 | 5/2011 | Baxter, III et al. | |
| 2011/0224702 A1 | 9/2011 | Van Kampen et al. | |
| 2011/0264149 A1 | 10/2011 | Pappalardo et al. | |
| 2012/0100200 A1 | 4/2012 | Belcheva et al. | |
| 2012/0160893 A1 | 6/2012 | Harris et al. | |
| 2012/0193391 A1 | 8/2012 | Michler et al. | |
| 2012/0209401 A1 | 8/2012 | Euteneuer et al. | |
| 2012/0211543 A1* | 8/2012 | Euteneuer ........ | A61B 17/07207 227/175.1 |
| 2012/0248171 A1 | 10/2012 | Bailly et al. | |
| 2012/0316608 A1 | 12/2012 | Foley | |
| 2013/0153627 A1 | 6/2013 | Euteneuer et al. | |
| 2013/0153628 A1 | 6/2013 | Euteneuer | |
| 2013/0158554 A1 | 6/2013 | Euteneuer et al. | |
| 2013/0158587 A1 | 6/2013 | Euteneuer et al. | |
| 2013/0158661 A1 | 6/2013 | Euteneuer et al. | |
| 2013/0172920 A1 | 7/2013 | Euteneuer et al. | |
| 2013/0172997 A1 | 7/2013 | Euteneuer et al. | |
| 2013/0184716 A1 | 7/2013 | Euteneuer et al. | |
| 2013/0240598 A1 | 9/2013 | Euteneuer et al. | |
| 2013/0245627 A1 | 9/2013 | Euteneuer et al. | |
| 2013/0245682 A1 | 9/2013 | Euteneuer et al. | |
| 2013/0245683 A1 | 9/2013 | Euteneuer et al. | |
| 2013/0245693 A1 | 9/2013 | Blain | |
| 2013/0245706 A1 | 9/2013 | Euteneuer et al. | |
| 2013/0245707 A1 | 9/2013 | Euteneuer et al. | |
| 2013/0245762 A1 | 9/2013 | Van Kampen et al. | |
| 2013/0245774 A1 | 9/2013 | Euteneuer et al. | |
| 2013/0304115 A1 | 11/2013 | Miyamoto | |
| 2014/0358163 A1 | 12/2014 | Farin et al. | |
| 2016/0073491 A1 | 3/2016 | Chen et al. | |
| 2016/0120542 A1 | 5/2016 | Westling et al. | |

FOREIGN PATENT DOCUMENTS

| | | | |
|---|---|---|---|
| EP | 0142225 | A1 | 5/1985 |
| EP | 0298400 | A1 | 1/1989 |
| EP | 0390613 | A1 | 10/1990 |
| EP | 0543499 | A1 | 5/1993 |
| EP | 0548998 | A1 | 6/1993 |
| EP | 0557963 | A1 | 9/1993 |
| EP | 0589306 | A2 | 3/1994 |
| EP | 0908152 | A1 | 4/1999 |
| EP | 0589306 | B1 | 8/1999 |
| EP | 1491157 | A1 | 12/2004 |
| EP | 1559379 | A1 | 8/2005 |
| EP | 1491157 | B1 | 11/2008 |
| EP | 2030576 | A2 | 3/2009 |
| GB | 2154688 | A | 9/1985 |
| GB | 2397240 | A | 7/2004 |
| JP | 58188442 | A | 11/1983 |
| JP | 2005586122 | A | 3/2005 |
| JP | 2006515774 | A | 6/2006 |
| JP | 2012514191 | A | 6/2012 |
| JP | 2012528699 | A | 11/2012 |
| WO | 8505025 | A1 | 11/1985 |
| WO | 0176456 | A2 | 10/2001 |
| WO | 0234140 | A2 | 5/2002 |
| WO | 03032815 | A2 | 4/2003 |
| WO | 2003105670 | A2 | 12/2003 |
| WO | 2004000138 | A1 | 12/2003 |
| WO | 2004062508 | A1 | 7/2004 |
| WO | 2004093690 | A1 | 11/2004 |
| WO | 2005016389 | A2 | 2/2005 |
| WO | 2006086679 | A1 | 8/2006 |
| WO | 2007014910 | A1 | 2/2007 |
| WO | 2007030676 | A2 | 3/2007 |
| WO | 2007078978 | A2 | 7/2007 |
| WO | 2007082088 | A2 | 7/2007 |
| WO | 2008065153 | A1 | 6/2008 |
| WO | 2008111073 | A2 | 9/2008 |
| WO | 2008111078 | A2 | 9/2008 |
| WO | 2008139473 | A2 | 11/2008 |
| WO | 2009079211 | A1 | 6/2009 |
| WO | 2009143331 | A1 | 11/2009 |
| WO | 2010141872 | A1 | 12/2010 |
| WO | 2010141907 | A1 | 12/2010 |
| WO | 2011095890 | A2 | 8/2011 |
| WO | 2011128903 | A2 | 10/2011 |
| WO | 2013007764 | A2 | 1/2013 |
| WO | 2013119321 | A1 | 8/2013 |

OTHER PUBLICATIONS

Alexander et al., "Ligament and tendon repair with an absorbable polymer-coated carbon fiber stent," Bulletin of the Hospital for Joint Diseases Orthopaedic Institute, 46(2):155-173, 1986.

Bahler et al., "Trabecular bypass stents decrease intraocular pressure in cultured himan anterior segments," Am. J. Opthamology, 138(6):988-994, Dec. 2004.

Chamay et al., "Digital contracture deformity after implantation of a silicone prosthesis: Light and electron microscopic study," The Journal of Hand Surgery, 3(3):266-270, May 1978.

D'Ermo et al., "Our results of the operation of ab externo," Opthalmologica, 168: 347-355, 1971.

France et al., "Biomechanical evaluation of rotator cuff fixation methods," The American Journal of Sports Medicine, 17(2), 1989.

Goodship et al., "An assessment of filamentous carbon fibre for the treatment of tendon injury in the horse," Veterinary Record, 106: 217-221, Mar. 8, 1980.

Hunter et al., "Flexor-tendon reconstruction in severely damaged hands," The Journal of Bone and Joint Surgery (American Volume), 53-A(5): 329-358, Jul. 1971.

Johnstone et al., "Microsurgery of Schlemm's canal and the human aqueous outflow system," Am. J. Opthamology, 76(6): 906-917, Dec. 1973.

Kowalsky et al., "Evaluation of suture abrasion against rotator cuff tendon and proximal humerus bone," Arthroscopy: The Journal of Arthroscopic and Related Surgery, 24(3):329-334, Mar. 2008.

Lee et al., "Aqueous-venous and intraocular pressure. Preliminary report of animal studies," Investigative Opthalmology, 5(1): 59-64, Feb. 1966.

(56) References Cited

OTHER PUBLICATIONS

Maepea et al., "The pressures in the episcleral veins, Schlemm's canal and the trabecular meshwork in monkeys: Effects of changes in intraocular pressure," Exp. Eye Res., 49:645-663, 1989.
Nicolle et al., "A silastic tendon prosthesis as an adjunct to flexor tendon grafting: An experimental and clinical evaluation," British Journal of Plastic Surgery, 22(3-4):224-236, 1969.
Rubin et al., "The use of acellular biologic tissue patches in foot and ankle surgery," Clinics in Podiatric Medicine and Surgery, 22:533-552, 2005.
Schultz, "Canaloplasty procedure shows promise for open-angle glaucoma in European study," Ocular Surgery News, 34-35, Mar. 1, 2007.
Spiegel et al., "Schlemm's canal implant: a new method to lower intraocular pressure in patients with POAG," Opthalmic Surgery and Lasers, 30(6):492-494, Jun. 1999.
Stenson et al., "Arthroscopic treatment of partial rotator cuff tears," Operative Techniques in Sports Medicine, 12 (2): 135-148, Apr. 2004.
Valdez et al., "Repair of digital flexor tendon lacerations in the horse, using carbon fiber implants," JAYMA, 177(5):427-435, Sep. 1, 1980.
Notification of Transmittal of the International Search Report and the Written Opinion of the International Searching Authority, or the Declaration, Mar. 7, 2016, 14 pages.

* cited by examiner

MEDICAL IMPLANT DELIVERY SYSTEM AND RELATED METHODS

CROSS REFERENCE TO RELATED APPLICATIONS

This application is a continuation of U.S. application Ser. No. 17/362,187, filed on Jun. 29, 2021, which is a continuation of U.S. application Ser. No. 16/170,603, filed on Oct. 25, 2018, which is a continuation of U.S. application Ser. No. 14/931,567, filed on Nov. 3, 2015, which claims the benefit of U.S. Provisional Patent Application Ser. No. 62/075,026 filed on Nov. 4, 2014, the disclosures of which are incorporated herein by reference. This application is also related to U.S. Provisional Patent Application Ser. No. 62/074,982 filed on Nov. 4, 2014, the disclosure of which is incorporated herein by reference.

TECHNICAL FILED

The present disclosure pertains generally, but not by way of limitation, to medical devices, and methods for using medical devices. More particularly, the present disclosure pertains to devices for introducing and positioning implants within patients, and methods for using such devices.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Adequate procedures do not exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. There is an ongoing need to deliver and adequately position medical implants during an arthroscopic procedure in order to treat injuries to the rotator cuff, rotator cuff tendons, or other soft tissue or tendon injuries throughout a body.

SUMMARY OF THE DISCLOSURE

The disclosure describes various medical devices and methods for using medical devices to assist in delivering, positioning, and securing implants within a body. In a first example, a fastener delivery tool configured to deliver a fastener into tissue of a patient may comprise a shaft, a handle assembly connected to a proximal end of the shaft, one or more prongs connected to a distal end of the shaft, and a fastener push rod received at least partially within the shaft, wherein the fastener push rod is connected to the handle assembly, wherein the fastener push rod is moveable relative to the shaft, and wherein the fastener push rod includes one or more detents configured to be received within a passageway of a fastener and secure the fastener to the fastener push rod with friction.

Alternatively or additionally, in another example, the fastener push rod may further comprise a plurality of arms connected to a distal end of the fastener push rod, and wherein the one or more detents are disposed on the plurality of arms.

Alternatively or additionally, in another example, the one or more prongs are formed from the shaft.

Alternatively or additionally, in another example, the one or more prongs comprise a concave surface.

Alternatively or additionally, in another example, the one or more prongs taper toward a tip of each prong.

Alternatively or additionally, in another example, the one or more prongs have a length that is between 50% and 120% the length of the fastener the fastener delivery system is configured to deliver into tissue of the patient.

Alternatively or additionally, in another example, a force applied to the handle assembly causes the fastener push rod to move relative to the shaft.

Alternatively or additionally, in another example, the handle assembly may comprise a housing, a trigger, and a bias member, wherein the bias member is connected to the housing and the trigger, wherein the bias member biases the trigger to a rest position, and wherein the force applied to the handle assembly comprises a force applied to the handle assembly to overcome a biasing force of the bias member.

In another example, a fastener delivery system may comprise a fastener delivery tool comprising a pilot member having a distal end and at least a pair of prongs extending from the distal end of the pilot member so that the prongs form pilot holes when the distal end of the pilot member is pressed against target tissue, and a fastener push rod disposed within at least a portion of the pilot member and moveable relative thereto. The fastener delivery system may further comprise a fastener carried by the fastener push rod, the fastener comprising a first arm having a proximal end and a distal end, and a second arm having a proximal end and distal end with a bridge extending from the proximal end of the first arm to the proximal end of the second arm, a first fluke of the fastener having a proximal end abutting the distal end of the first arm, and a second fluke of the fastener having a proximal end abutting the distal end of the second arm, and wherein each of the at least a pair of prongs comprise a curved inner surface.

Alternatively or additionally, in another example, each of the first fluke and the second fluke define a passageway extending at least partially through each fluke, with each passageway defining at least one surface.

Alternatively or additionally, in another example, the fastener push rod comprises at least a pair of arms, and wherein each of the at least a pair of arms is configured to be received within a passageway of the first fluke or the second fluke.

Alternatively or additionally, in another example, each arm further comprises a detent, and wherein when each arm is received within a passageway, each detent presses against the at least one surface of the passageway and retains the fastener on the fastener push rod by friction.

Alternatively or additionally, in another example, each of the first fluke and the second fluke have defined heights, and wherein each of the at least a pair of prongs tapers toward a distal end of the prong such that a width of at least a portion of each prong is less than the defined height of the first fluke or the second fluke.

Alternatively or additionally, in another example, a first width of at least a portion of each prong is between 85% and 95% of the defined height of the first fluke or the second fluke.

Alternatively or additionally, in another example, a second width of at least a portion of each prong is between 60% and 75% of the defined height of the first fluke or the second fluke.

Alternatively or additionally, in another example, each of the at least a pair of prongs have a length that is between 50% and 120% the length of the fastener.

Alternatively or additionally, in another example, the one or more prongs are formed from the pilot member.

In still another example, a method for deploying a fastener into target tissue may comprise positioning a fixation tool shaft proximate the target tissue, the fixation tool shaft having one or more prongs disposed proximate a distal end of the fixation tool shaft, wherein a fastener push rod is disposed at least partially within the fixation tool shaft, the fastener push rod comprising one or more arms, each arm having a detent disposed thereon, the fastener push rod further carrying a fastener, wherein the fastener is retained on the one or more arms by friction between the detents and the fastener, and wherein the fixation tool shaft is coupled to a handle assembly, the handle assembly comprising a trigger; applying force to the fixation tool shaft in the direction of the target tissue, causing the prongs to pierce the target tissue creating a pilot holes; applying force to the trigger thereby causing the fastener push rod to move distally relative to the fixation tool shaft and causing the one or more arms and the fastener to move into the pilot holes; and removing the one or more arms and the prongs from the pilot holes.

Alternatively or additionally, in another example, the one or more prongs comprise a concave surface.

Alternatively or additionally, in another example, the one or more prongs taper toward a tip of each prong.

The above summary of some examples is not intended to describe each disclosed example device, component, or method or every implementation of the present disclosure. The Brief Description of the Drawings, and Detailed Description, which follow, more particularly exemplify these examples, but are also intended as exemplary and not limiting.

DETAILED DESCRIPTION

Figure 1:
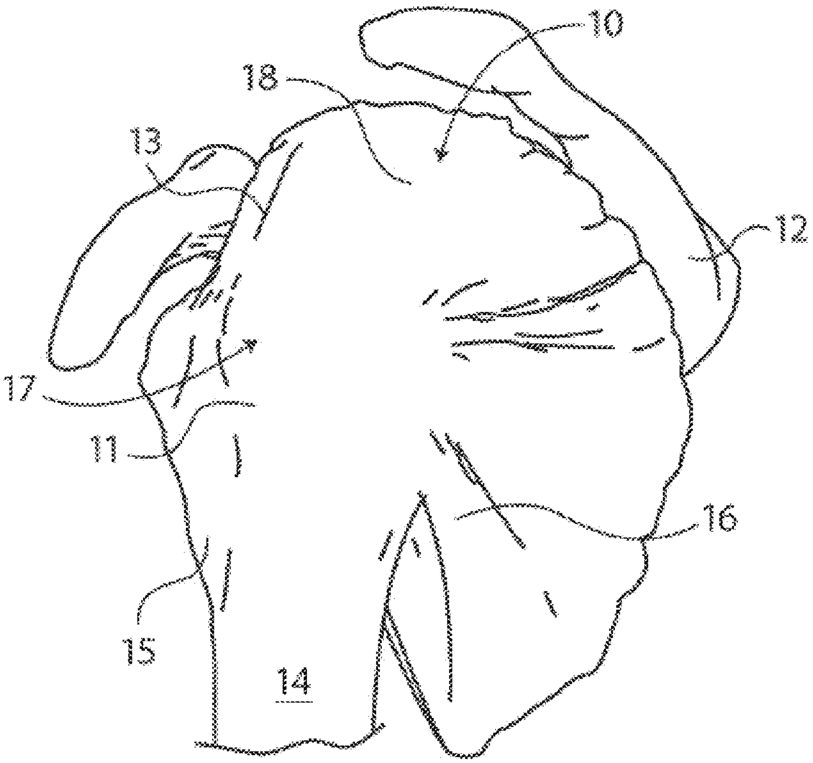
FIG. 1 is a simplified perspective view of the human rotator cuff and associated anatomical structure.

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate examples of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant Figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", "an example", "some examples", "other examples", etc., indicate that the embodiment(s) and/or example(s) described may include a particular feature, structure, or characteristic, but every embodiment may not necessarily include the particular feature, structure, or characteristic. Moreover, such phrases are not necessarily referring to the same embodiment and/or example. Further, when a particular feature, structure, or characteristic is described in connection with an embodiment and/or example, it would be within the knowledge of one skilled in the art to affect such feature, structure, or characteristic in connection with other embodiments and/or examples, whether or not explicitly described, unless clearly stated to the contrary. That is, the various individual features described below, even if not explicitly shown in a particular combination, are nevertheless contemplated as being combinable or able to be arranged with each other to form other additional embodiments and/or examples or to complement and/or enrich the described embodiment(s) and/or example(s), as would be understood by one of ordinary skill in the art.

FIG. 1 illustrates an example of a rotator cuff, including muscles 10 which are a complex of four muscles. These four muscles are the supraspinatus, the infraspinatus, the subscapularis, and the teres minor. The four muscles of the rotator cuff arise from the scapula 12. The distal tendons of the rotator cuff muscles splay out and interdigitate to form a common continuous insertion on the humerus 14 and humerus head 17. The subscapularis 16 arises from the anterior aspect of the scapula 12 and attaches over much of the lesser tuberosity of humerus 14. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The teres minor 15 arises from the lower lateral aspect of the scapula 12 and attaches to the lower aspect of the greater tuberosity 11.

Figure 2:
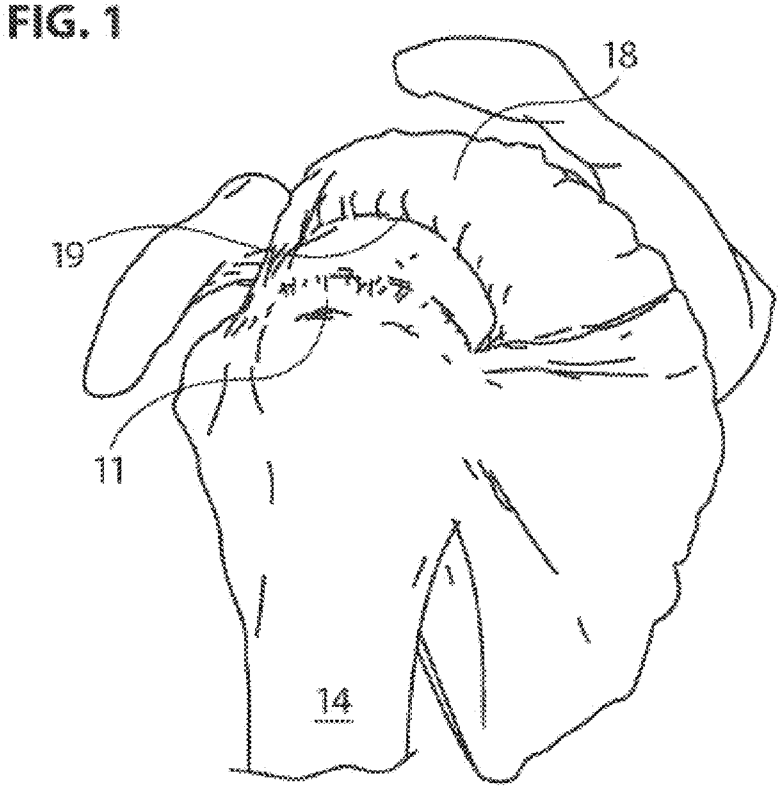
FIG. 2 is a schematic depiction of a full thickness tear in the supraspinatus tendon of the rotator cuff of FIG. 1.

The rotator cuff muscles 10 are critical elements for maintaining shoulder muscle balance in order to effectuate movement of the shoulder joint. With its complexity, range of motion and extensive use, a fairly common soft tissue injury is damage to the rotator cuff or rotator cuff tendons. Damage to the rotator cuff is a potentially serious medical condition that may occur during hyper-extension, from an acute traumatic tear or from overuse of the joint. A tear in the supraspinitus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear.

Current accepted treatment for a full thickness tear or a partial thickness tear greater than 50% includes reconnecting the torn tendon via sutures. The procedure generally includes completing the tear to a full thickness tear by cutting the tendon prior to reconnection. In contrast to the treatment of a full thickness tear or a partial thickness tear of greater than 50%, the treatment for a partial thickness tear less than 50% usually involves physical cessation from use of the tendon, i.e., rest. Specific exercises can also be prescribed to strengthen and loosen the shoulder area. However, in many instances, whether after treatment for a partial thickness tear greater than 50% or less than 50%, the shoulder does not heal fully and the patient can be left with a source of chronic pain and stiffness, along with preventing the patient from recovering full range of motion.

As described above, current treatments do not currently exist for repairing partial thickness tears of the supraspinatus tendon. The present disclosure details techniques and devices for treating partial thickness tears which help prevent future tendon damage by strengthening or repairing the native tendon having the partial thickness tear.

Figure 3:
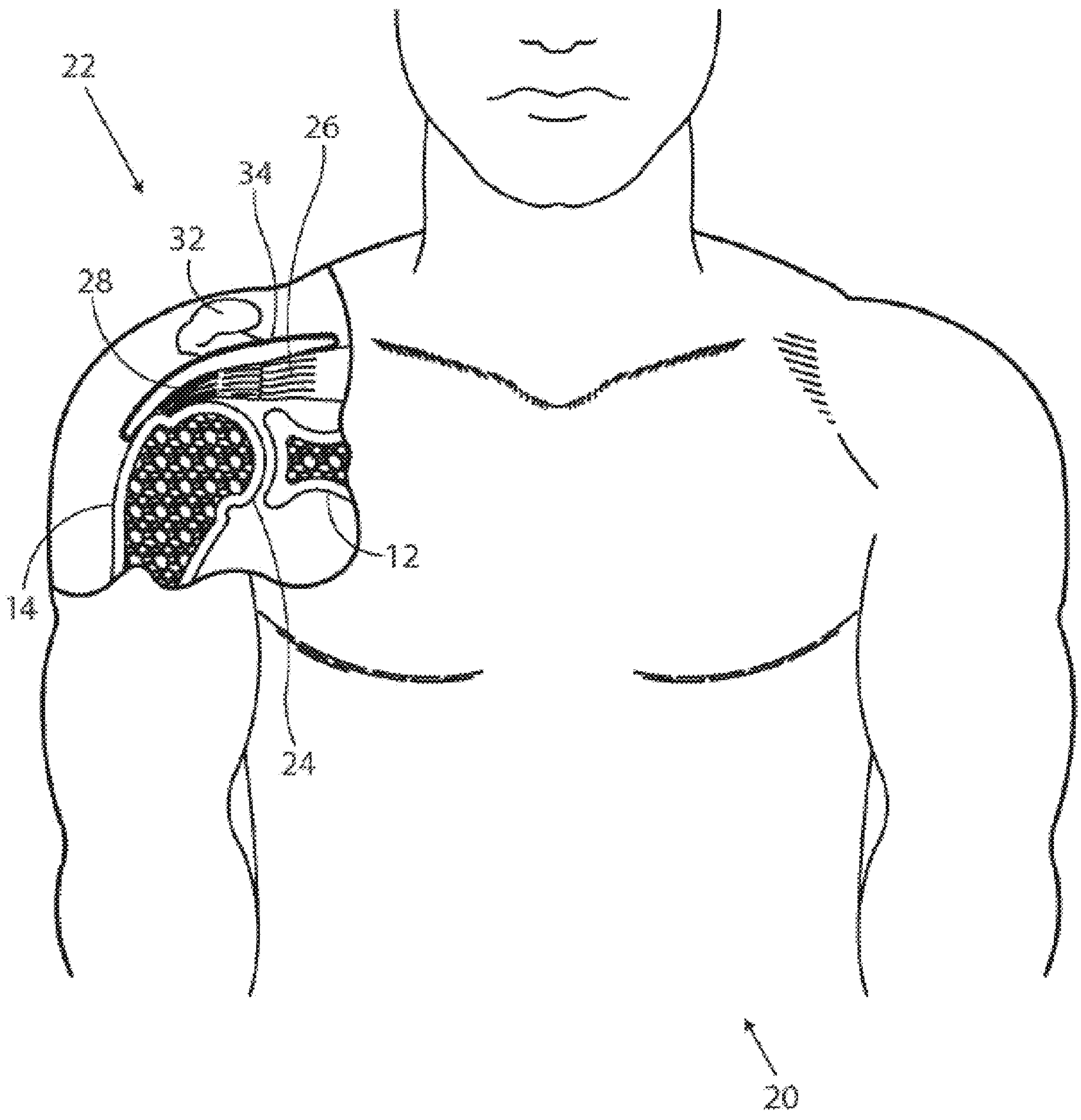
FIG. 3 is a stylized anterior view of a patient with a should of the patient being shown in cross-section.

FIG. 3 is a stylized anterior view of a patient 20. For purposes of illustration, a shoulder 22 of patient 20 is shown in cross-section in FIG. 3. Shoulder 22 includes a humerus 14 and a scapula 12. In FIG. 3, a head 24 of humerus 14 can be seen mating with a glenoid fossa of scapula 12 at a glenohumeral joint. With reference to FIG. 3, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 3.

With reference to FIG. 3, it will be appreciated that a distal tendon 28 of the supraspinatus 26 meets humerus 14 at an insertion point. Scapula 12 of shoulder 22 includes an acromium 32. In FIG. 3, a subacromial bursa 34 is shown extending between acromium 32 of scapula 12 and head 24 of humerus 14. In FIG. 3, subacromial bursa 34 is shown overlaying supraspinatus 26. Subacromial bursa 34 is one of the hundreds of bursae found the human body. Each bursa comprises a fluid filled sac. The presence of these bursae in the body reduces friction between bodily tissues. Injury and/or infection of the bursa can cause it to become inflamed. This condition is sometimes referred to as bursitis.

The exemplary methods and apparatus described herein may be used to fix tendon repair implants to various target tissues. For example, a tendon repair implant may be fixed to one or more tendons associated with an articulating joint, such as the glenohumeral joint. The tendons to be treated may be torn, partially torn, have internal micro-tears, be un-torn, and/or be thinned due to age, injury or overuse. The disclosed methods and apparatus and related devices may provide beneficial therapeutic effect on a patient experiencing joint pain believed to be caused by partial thickness tears and/or internal micro-tears. By applying a tendon repair implant early before a full tear or other injury develops, the implant may cause the tendon to thicken and/or at least partially repair itself, thereby avoiding more extensive joint damage, pain, and the need for more extensive joint repair surgery.

Figure 4:
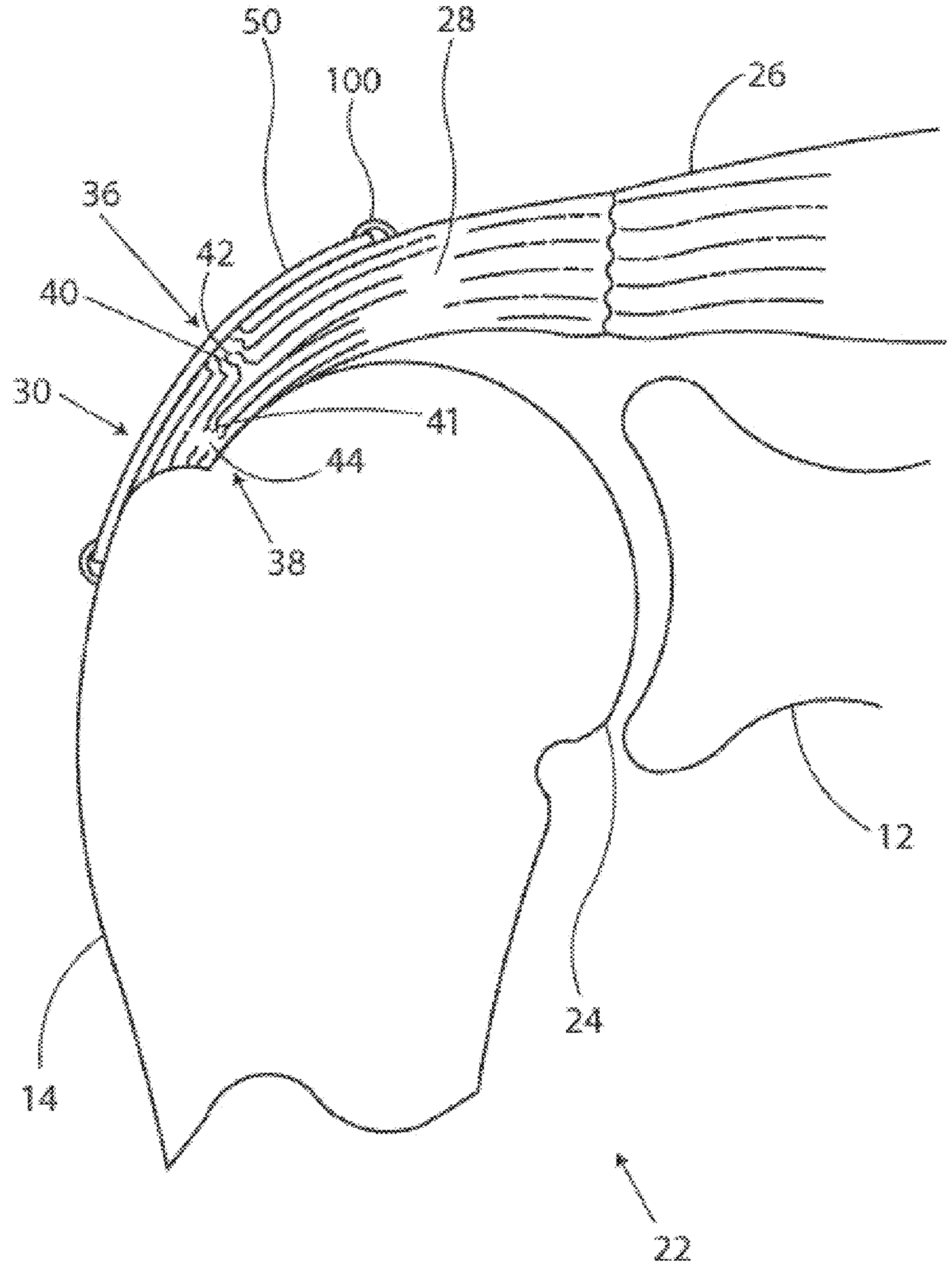
FIG. 4 is a stylized anterior view of a shoulder including a humerus and a scapula, with the head of the humerus mating with the glenoid fossa of the scapula at a glenohumeral joint and a sheet-like material is fixed to the supraspinatus tendon.

FIG. 4 is a stylized anterior view of a shoulder 22 including a humerus 14 and a scapula 12. In FIG. 4, a head 24 of humerus 14 is shown mating with a glenoid fossa of scapula 12 at a glenohumeral joint. A supraspinatus 26 is also shown in FIG. 4. This muscle (along with others) controls the movement of humerus 14 relative to scapula 12. A distal tendon 28 of supraspinatus 26 meets humerus 14 at an insertion.

In the embodiment of FIG. 4, distal tendon 28 includes a first damaged portion 36. A number of loose tendon fibers 40 in first damaged portion 36 are visible in FIG. 4. First dam-aged portion 36 includes a first tear 42 extending partially through distal tendon 28. First tear 42 may therefore be referred to as a partial thickness tear. With reference to FIG. 4, it will be appreciated that first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 4, it will be appreciated that distal tendon 28 includes a second damaged portion 38 located near insertion point 30. In the embodiment of FIG. 4, second damaged portion 38 of distal tendon 28 has become frayed and a number of loose tendon fibers 41 are visible in FIG. 4. Second damaged portion 38 of distal tendon 28 includes second tear 44. With reference to FIG. 4, it will be appreciated that second tear 44 begins on the side of distal tendon 28 facing the humerus 14. Accordingly, second damaged portion 38 may be referred to as an articular side tear.

In the embodiment of FIG. 4, a sheet-like implant 50 has been placed over the bursal side of distal tendon 28. With reference to FIG. 4, it will be appreciated that sheet-like implant 50 extends over insertion point 30, first tear 42, and second tear 44. Some useful methods in accordance with this detailed description may include placing a tendon repair implant on the bursal side of a tendon regardless of whether the tears being treated are on the bursal side, articular side, or within the tendon. In some cases the exact location and nature of the tears being treated may be unknown. A tendon repair implant may be applied to the bursal side of a tendon to treat shoulder pain that is most likely caused by one or more partial thickness tears in the tendon. In the embodiment of FIG. 4, sheet-like implant 50 is fixed to distal tendon 28 and to humerus 14 by a plurality of staples 100 as described herein in detail. In alternative examples, sheet-like implant 50 may be fixed only to distal tendon 28 by plurality of staples 100. The strain imparted on sheet-like implant 50 may differ in examples where sheet-like implant 50 is affixed only to distal tendon 28 and examples where sheet-like implant 50 is affixed to both distal tendon 28 and humerus 14, and some injuries or patients may respond more advantageously to one or the other of these fixation methods.

Figure 5:
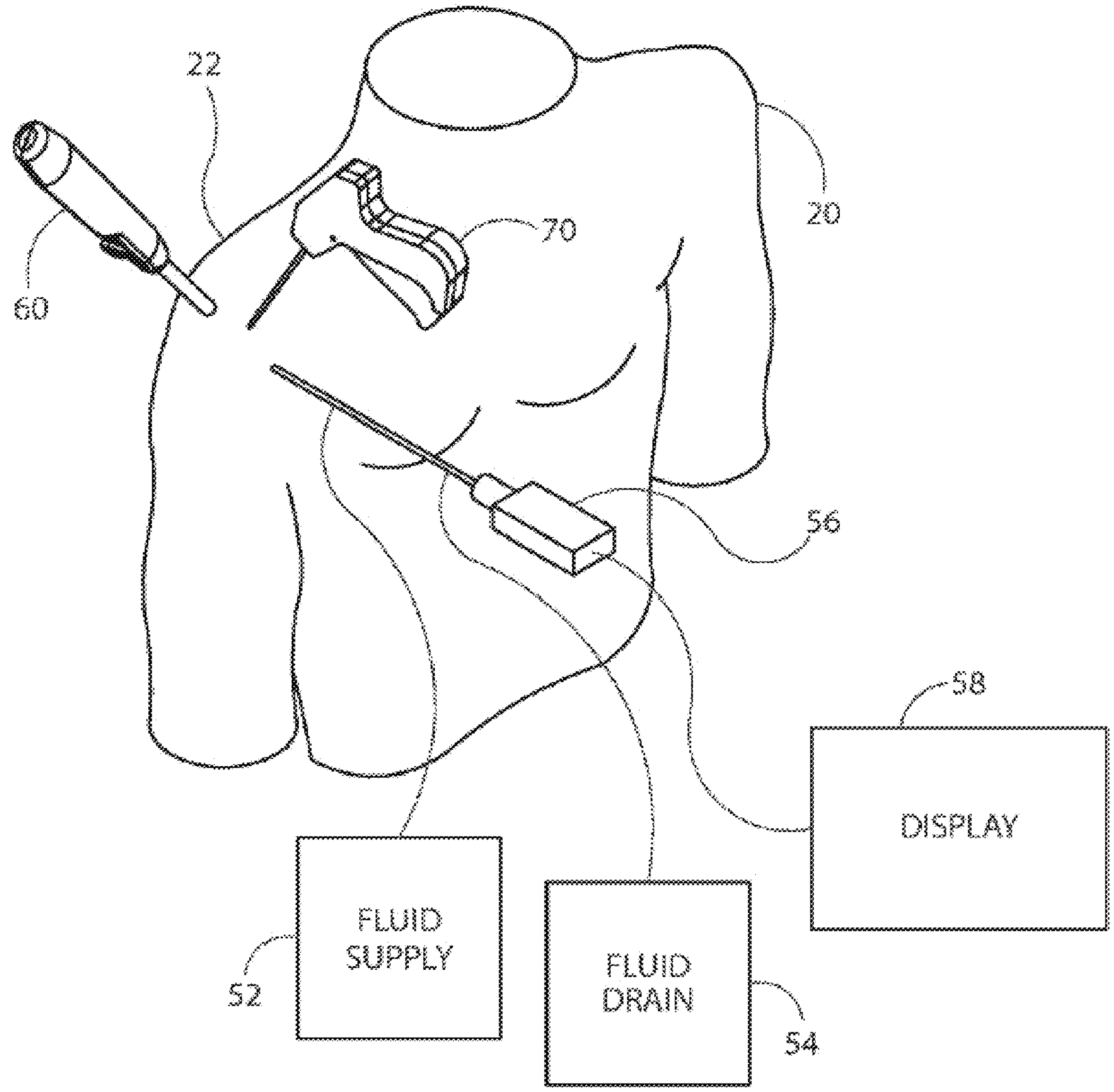
FIG. 5 is a stylized perspective view illustrating an exemplary procedure for treating a shoulder of a patient.

FIG. 5 is a stylized perspective view illustrating an exemplary procedure for treating a shoulder 22 of a patient 20. The procedure illustrated in FIG. 5 may include, for example, fixing tendon repair implants to one or more tendons of shoulder 22. The tendons treated may be torn, partially torn, have internal micro-tears, be un-torn, and/or be thinned due to age, injury or overuse.

Shoulder 22 of FIG. 5 has been inflated to create a cavity therein. In the exemplary embodiment of FIG. 5, a fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be fixed to a bursal surface of the tendon regardless of whether there are visible signs of tendon damage.

A delivery system 60 can be seen extending from shoulder 22 in FIG. 5. Delivery system 60 comprises a sheath that is fixed to a handle. The sheath defines a lumen and a distal opening fluidly communicating the lumen. In the example of FIG. 5, the distal opening of the sheath has been placed in fluid communication with the cavity created in shoulder 22.

A tendon repair implant is at least partially disposed in the lumen defined by the sheath of delivery system 60. Delivery system 60 can be used to place the tendon repair implant inside shoulder 22. Delivery system 60 can also be used to hold the tendon repair implant against the tendon. In some embodiments, the tendon repair implant is folded into a compact configuration when inside the lumen of the sheath of delivery system 60. When this is the case, delivery system 60 may be used to unfold the tendon repair implant into an expanded shape.

The tendon repair implant may be fixed to the tendon while it is held against the tendon by delivery system 60. Various attachment elements may be used to fix the tendon repair implant to the tendon. Examples of attachment elements that may be suitable in some applications include sutures, tissue anchors, bone anchors, and staples. In the example of FIG. 5, the shaft of a fixation tool 70 is shown extending into shoulder 22. In one example, fixation tool 70 is capable of fixing the tendon repair implant to the tendon with one or more staples while the tendon repair implant is held against the tendon by delivery system 60.

Figure 6:
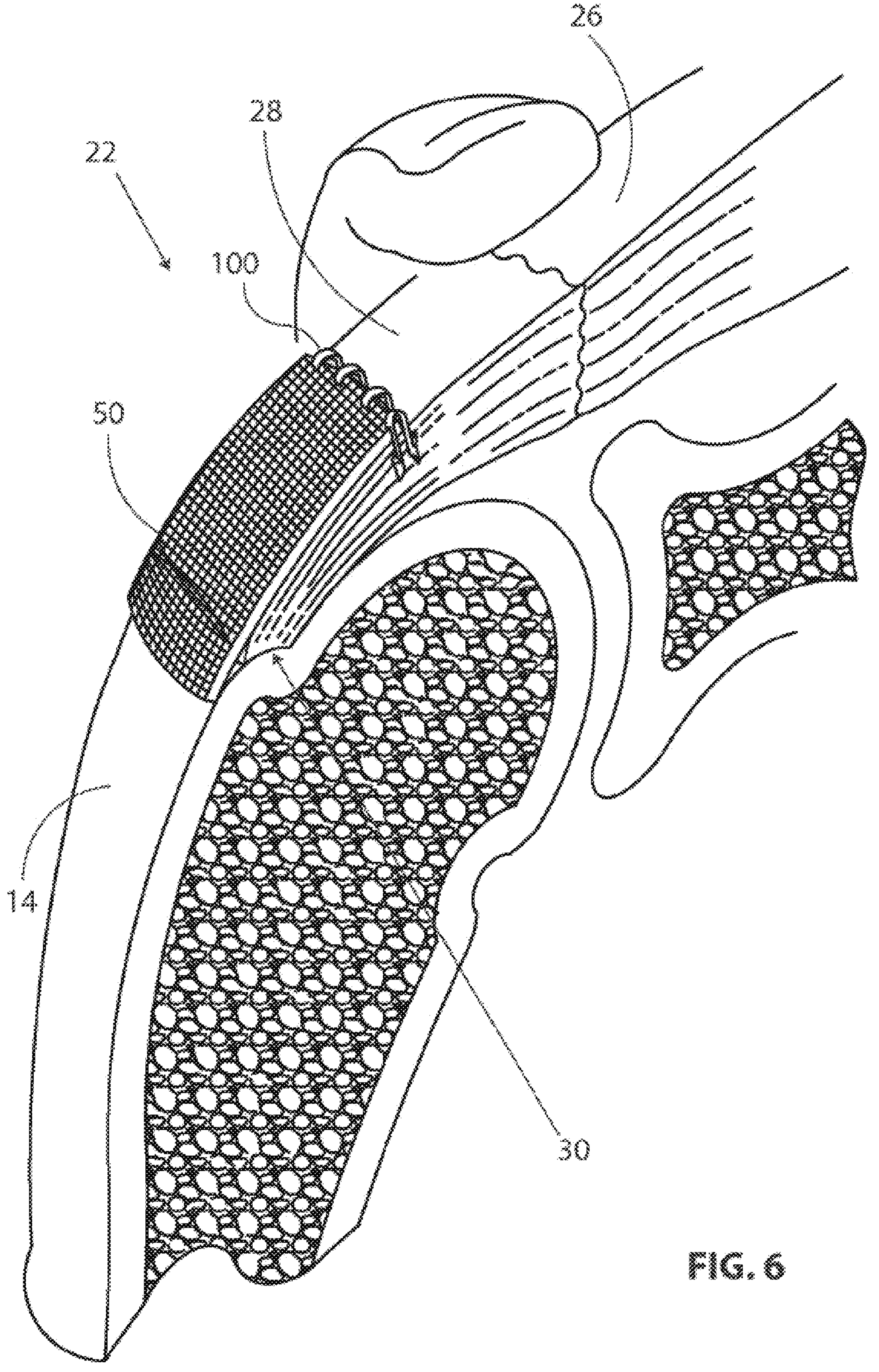
FIG. 6 is a stylized perspective view of a shoulder including a distal tendon having a tear with a sheet-like material affixed thereto.

FIG. 6 is a stylized perspective view of a shoulder 22 including a supraspinatus 26 having a distal tendon 28. With reference to FIG. 6, it will be appreciated that a tendon repair implant 50 has been fixed to a surface of distal tendon 28. Tendon repair implant 50 may comprise, for example, various sheet-like structures without deviating from the spirit and scope of the present detailed description. In some useful examples, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications include weaving, knitting, and braiding. In some examples, the sheet-like structure may comprise a laminate including multiple layers of film with each layer of film defining a plurality of micro-machined or formed holes. The sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Freemont, Calif. which identifies these materials using the trademark BIOMATE-RIAL™.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the example of FIG. 6, a plurality of staples 100 are fixing tendon repair implant 50 to distal tendon 28. In some exemplary methods, a plurality of staples 100 may be applied using a fixation tool. The fixation tool may then be withdrawn from the body of the patient.

Distal D tendon 28 meets humerus 14 at an insertion point 30. With reference to FIG. 6, it will be appreciated that sheet-like implant 50 extends over insertion point 30. Tendon repair implant may be applied to distal tendon 28, for example, using the procedure illustrated in FIG. 5. Alternatively, in examples where sheet-like implant 50 is not fixed to humerus 14, sheet-like implant 50 may not extend over insertion point 30. Rather, the whole of sheet-like implant 50 may generally extend along and over distal tendon 28.

Figure 7C:
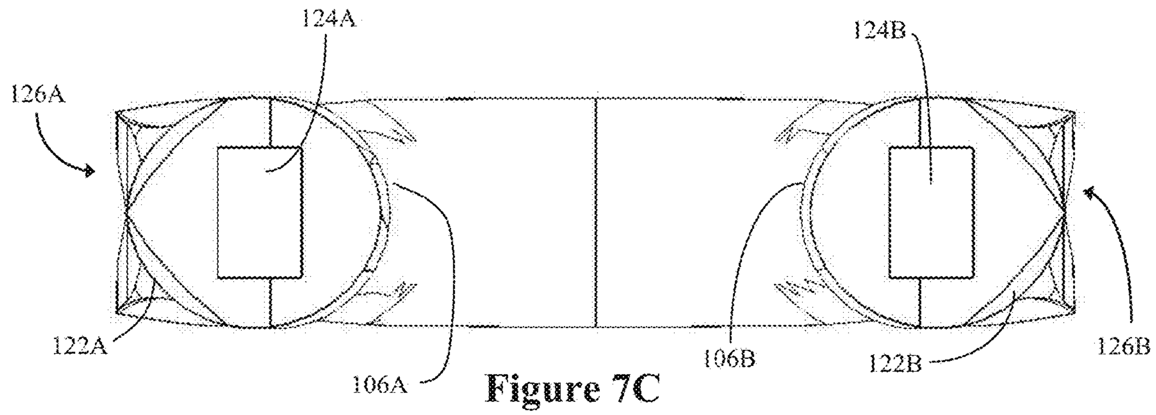
FIGS. 7A-7C are multiple plan views illustrating an exemplary fastener or staple in accordance with the present disclosure.
Figure 7A:
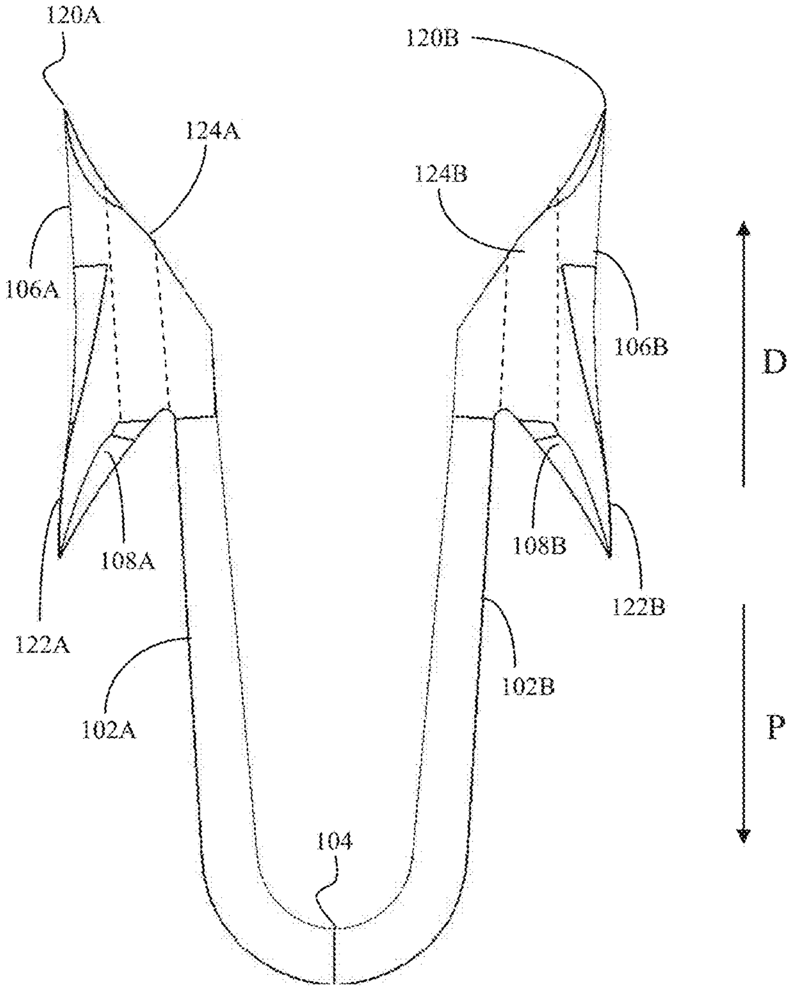
Figure 7B:
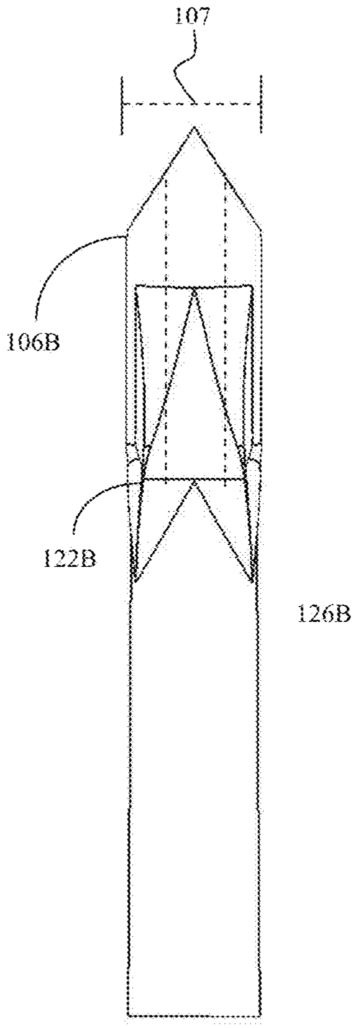

FIG. 7A, FIG. 7B, and FIG. 7C are multiple plan views illustrating an exemplary staple 100 in accordance with the present disclosure. A proximal direction is illustrated with an arrow P in FIGS. 7A-C. A distal direction is illustrated with a second arrow D in FIGS. 7A-C.

Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIGS. 7A-C, first fluke 106A and second fluke 106B are shown extending distally from first arm 102A and second arm 102B, respectively. With reference to FIGS. 7A-C, it will be appreciated that first fluke 106A has a lateral extent that is larger than a lateral extent of first arm 102A. Additionally, each fluke has a height dimension as evidenced by height 107. First fluke 106A is mounted eccentrically to first arm 102A in the embodiment of FIGS. 7A-C. Second fluke 106B is mounted eccentrically to second arm 102B and second fluke 106B has a lateral extent that is larger than a lateral extent of second arm 102B. First fluke 106A includes a first proximal surface 108A projecting at an outward angle in a proximal direction away from the distal end of first arm 102A. Second fluke 106B includes a second proximal surface 108B projecting at an outward angle in a proximal direction away from the distal end of second arm 102B.

With reference to FIG. 7A, it will be appreciated that first fluke 106A includes a first point 120A and a first barb 122A. Second fluke 106B includes a second point 120B and a second barb 122B. In FIGS. 7A-C, first point 120A and second point 120B are shown generally pointing in the distal direction indicated by arrow D. Also in FIGS. 7A-C, first barb 122A and second barb 122B are shown generally pointing in the proximal direction indicated by arrow P. Generally, the tips of first barb 122A and second barb 122B may be the outward most portions of staple 100.

With reference to FIG. 7A it will be appreciated that first fluke 106A defines a first passageway 124A and second fluke 106B defines a second passageway 124B. In the examples of FIGS. 7A-C, first passageway 124A extends through first fluke 106A and second passageway 124B extends through second fluke 106B. It will be appreciated, however, that first passageway 124A may extend through other portions of staple 100 in other examples. Similarly, second passageway 124B may extend through other portions of staple 100 in other examples. With reference to FIG. 7B it will be appreciated that, first passageway 124A and second passageway 124B each have a generally square cross-sectional shape defining multiple opposing surfaces. First passageway 124A and second passageway 124B, however, may have various cross-sectional shapes in other examples, such as circular or oval cross-sectional shapes, without deviating from the spirit and scope of the present disclosure. Further, each passageway can extend partially through the length of each fluke rather than all the way through to provide a cavity rather than a passageway.

Additionally, each of first passageway 124A and second passageway 124B also have a defined cross-sectional width and/or diameter. For example, as illustrated in FIGS. 7A-C, first passageway 124A and second passageway 124B define passageways with rectangular or square cross-sections. The rectangular or square cross-sections have defined width and height dimensions, where the height dimension may be measured between each of the top and bottom opposing surfaces of first passageway 124A and second passageway 124B, as seen from the perspective of FIG. 7C. The width dimension of the rectangular or square cross-sections may be measured between each of the left and right opposing faces of first passageway 124A and second passageway 124B, as seen from the perspective of FIG. 7C. Some example height dimensions that first passageway 124A and second passageway 124B may have include dimensions in the range of between 0.0175 inches (0.445 millimeters) and 0.026 inches (0.661 millimeters). Some example width dimensions that first passageway 124A and second passageway 124B may have include dimensions in the range of between 0.0135 inches (0.343 millimeters) and 0.022 inches (0.559 millimeters).

With reference to FIG. 7C, it will be appreciated that first barb 122A of first fluke 106A defines a first notch 126A. In the example of FIGS. 7A-C, first notch 126A divides first barb 122A into a first sub-barb and a second sub-barb. Second barb 122B of second fluke 106B defines a second notch 126B. In the example of FIGS. 7A-C, second notch 126B divides second barb 122B into a first sub-barb and a second sub-barb.

Figure 8:
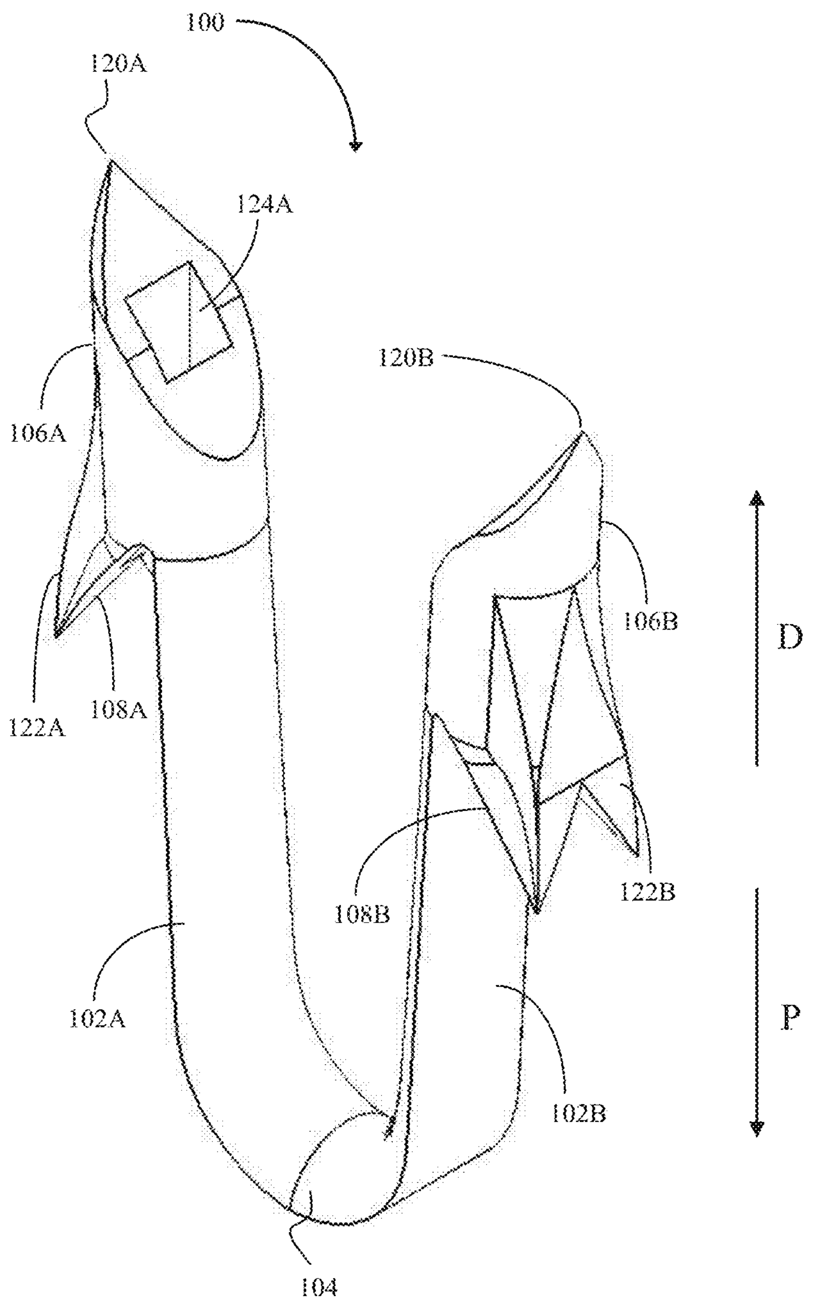
FIG. 8 is a perspective view further illustrating the fastener or staple shown in the previous FIGS. 7A-7C.

FIG. 8 is a perspective view showing staple 100 shown in FIGS. 7A-C. Many of the features of staple 100 described with respect to FIGS. 7A-C can also be seen in FIG. 8, including first arm 102A, second arm 102B, bridge 104, first fluke 106A, first passageway 124A, among others.

Figure 9:
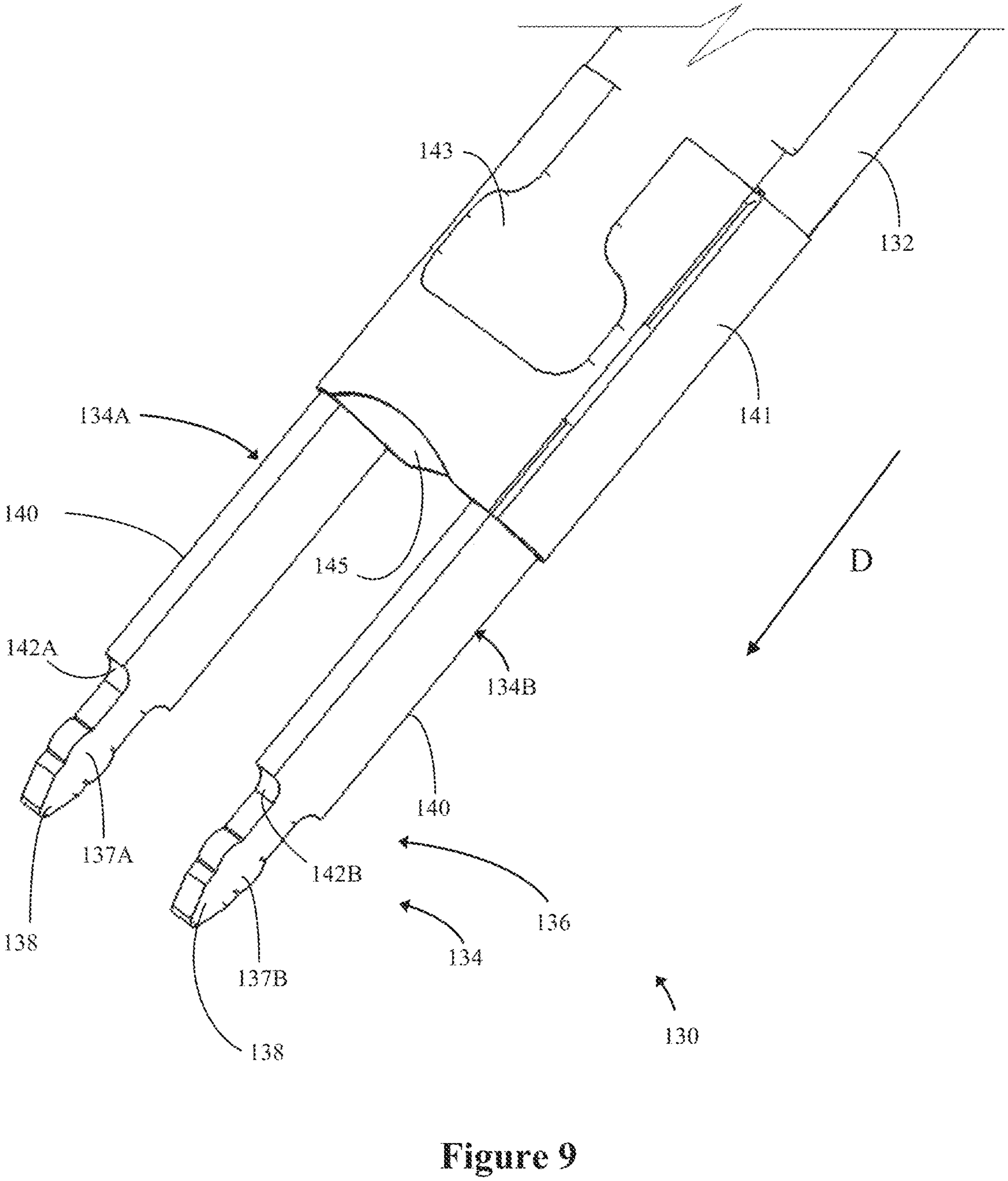
FIG. 9 is a perspective view showing a staple push rod that may be used in conjunction with the fastener or staple shown in FIGS. 7A-7C and FIG. 8.

FIG. 9 is a perspective view showing a staple push rod 130 that may be used in conjunction with staple 100 shown in FIGS. 7A-C and 8. Staple push rod 130 includes a shaft 132 and a pair of arms 134 extending distally beyond a distal end of shaft 132. The distal direction is indicated with an arrow D in FIG. 9. In some examples, shaft 130 and arms 134 may be formed in two separate pieces. For instance, as seen in FIG. 9, arms 130 are attached together as part of distal piece 141. In examples where shaft 130 and arms 134 are formed in separate pieces, distal piece 141 may have a connecting means at the proximal end of distal piece 141, and shaft 130 may have corresponding connecting means 143 attached to the distal end of shaft 130. In some examples, distal piece 141 may include a shaped hole or groove and connecting means 143 may have a matching shape that slots into the shaped hole or groove, as in FIG. 9. However, various other means and methods for connecting distal piece 141 to shaft 132 are contemplated in other examples.

Arms 134 include a first arm 134A and a second arm 134B. First arm 134A and second arm 134B form a fork 136. In the example of FIG. 9, each arm 134A, 134B has a distal portion 138 and a proximal portion 140. In some examples, each distal portion 138 is dimensioned to extend into a passage defined by a staple, for example first passageway 124A and second passageway 124B of staple 100. In some examples, each arm 134A, 134B may additionally have detents 137A, 137B, respectively. Detents 137A, 137B may have a generally circular shape and have a diameter sized appropriately to the height dimensions of first passageway 124A and second passageway 124B. More specifically, the diameter of detents 137A, 137B may be sized to be slightly larger than the height dimension of first passageway 124A and second passageway 124B. In such examples, in order for detents 137A, 137B to enter first passageway 124A and second passageway 124B, a small amount of force may need to be applied to push detents 137A, 137B into the passageways. In such examples, detents 137A, 137B and/or staple 100 may be made from a material that has a level of rigidity where, in response to detents 137A, 137B being pushed into passageways 124A, 124B, detents 137A, 137B and/or passageways 124A, 124B of staple 100 deform slightly. The slight deformation would thereby allow detents 137A, 137B to be pushed into passageways 124A, 124B.

Once disposed in passageways 124A, 124B, detents 137A, 137B may press against the surfaces of passageways 137A, 137B and hold onto staple 100 due to the friction between detents 137A, 137B and passageways 124A, 124B. An example range of diameters of detents 137A, 137B includes diameters between 0.019 inches (0.483 millimeters) and 0.029 inches (0.737 millimeters). Although depicted in FIG. 9 as generally circular, in other examples detents 137A, 137B may be shaped differently yet still allow for a friction fit between detents 137A, 137B and passageways 124A, 124B when disposed therein. For example, detents 137A, 137B may be half-circular, oval or half oval, triangular, or any other suitable shape.

Of course, in other examples, detents 137A, 137B may generally comprise other shapes. For instance, instead of having a generally circular shape, detents 137A, 137B may have an ovular, triangular, pyramidal, trapezoidal, or other shape. The specific shape of detents 137A, 137B, and more specifically, the shape of the portion of detents 137A, 137B that contact passageways 124A, 124B may be chosen so that a specific area of detents 137A, 137B contacts passageways 124A, 124B, where a relatively greater area imparts relatively greater friction force between detents 137A, 137B and passageways 124A, 124B, and a relatively lesser area imparts relatively lesser friction force between detents 137A, 137B and passageways 124A, 124B.

In the example of FIG. 9, each proximal portion 140 has a width larger than a width of each distal portion 138. In some examples, shoulders 142A, 142B of first arm 134A and second arm 134B, respectively, may contact proximal surfaces 108A, 108B of the staple and apply pushing forces thereto. However, in other examples, shoulders 142A, 142B are disposed in a more proximal direction such when a staple is disposed on fork 136, bridge 104 of the staple contacts bridge 145 of fork 136 before either of shoulders 142A, 142B contact proximal surfaces 108A, 108B. In such examples, the pushing forces applied to the staple are applied to bridge 104 of the staple by bridge 145 of fork 136 rather than to proximal surfaces 108A, 108B by shoulders 142A, 142B.

In the example of FIG. 9, proximal portion 140 of first arm 134A and the proximal portion 140 of second arm 134B extend generally parallel in distal direction D away from shaft 132. In examples where pushing forces are applied through bridge 145 rather by through shoulders 142A, 142B, arms 134A, 134B may generally act as guides for staple flukes 106A, 106B as staple 100 is advanced into patient tissue.

Figure 10A:
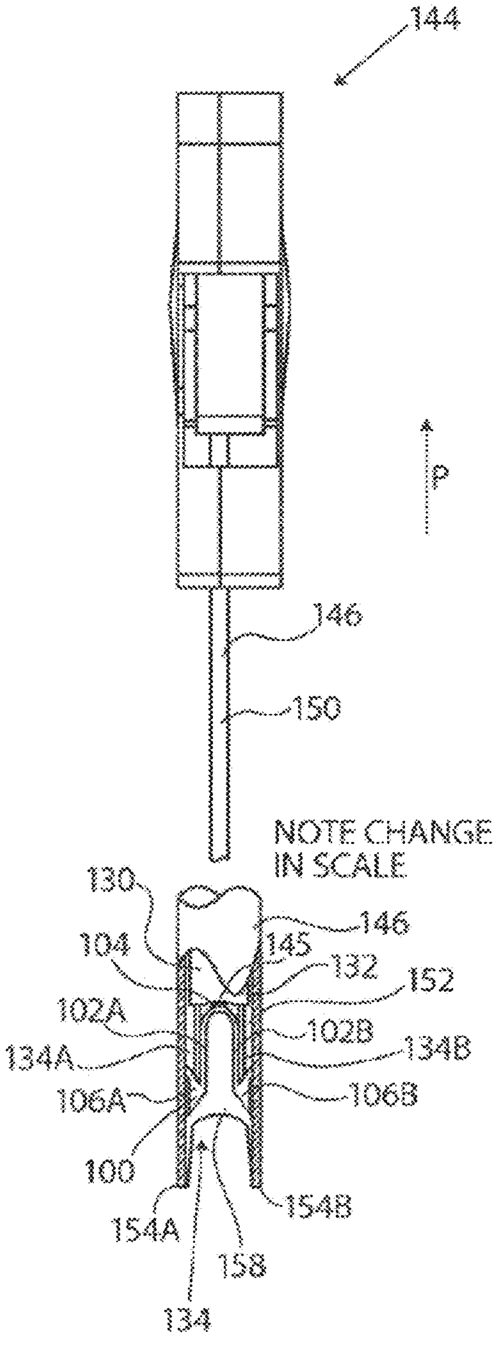
FIGS. 10A-10B illustrate multiple plan views of an exemplary fixation tool in accordance with the present disclosure.
Figure 10B:
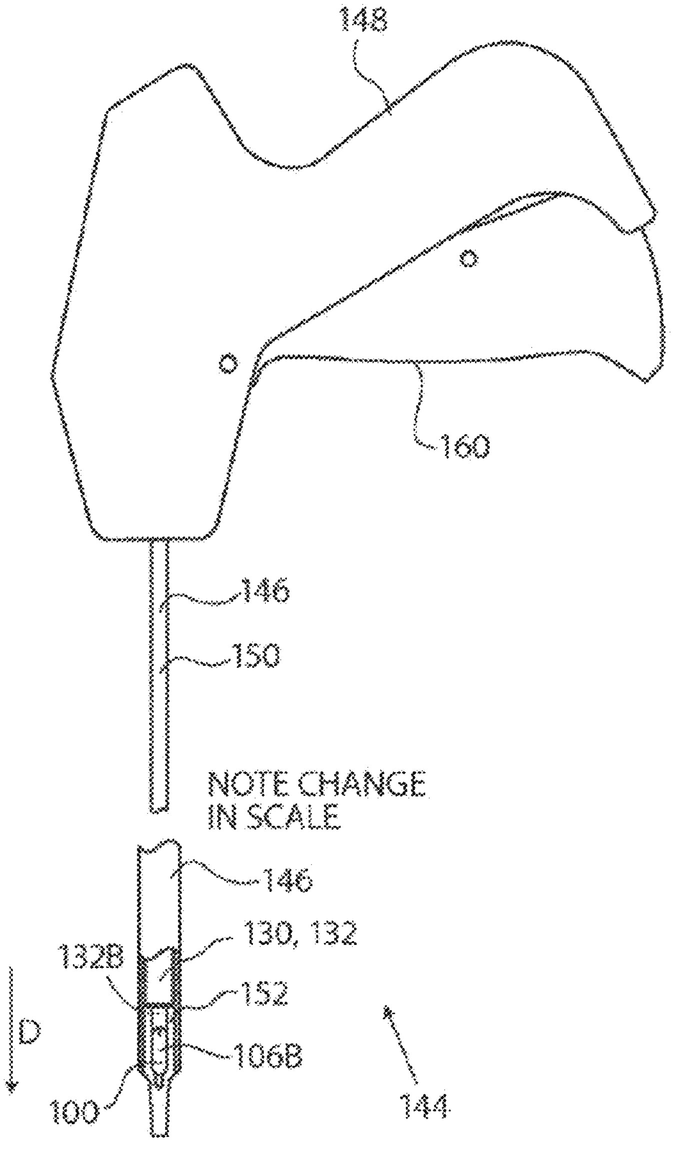

FIG. 10A and FIG. 10B illustrate multiple plan views of an exemplary fixation tool 144 in accordance with the present disclosure. Fixation tool 144 incorporates staple push rod 130 and may be operated to deliver staple 100 into tissue. FIG. 10A may be referred to as a top view of fixation tool 144 and FIG. 10B may be referred to as a side view of fixation tool 144. In the embodiment of FIGS. 10A-B, fixation tool 144 comprises a pilot member or fixation tool shaft 146 that is attached to a handle 148. Fixation tool shaft 146 comprises a wall 150 defining a lumen 152. With reference to FIGS. 10A-B, it will be appreciated that fixation tool shaft 146 includes a first prong 154 and a second prong 156 that extend distally beyond a distal end 158 of lumen 152.

In FIGS. 10A-B, a staple 100 can be seen residing in lumen 152 of fixation tool shaft 146. For purposes of illustration, a distal portion of fixation tool shaft 146 is enlarged in FIGS. 10A-B to better show staple 100. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIGS. 10A-B, first fluke 106A and second fluke 106B are shown extending distally from first arm 102A and second arm 102B, respectively.

Staple push rod 130 includes a shaft 132, bridge 145, and a pair of arms 134 extending distally beyond a distal end of shaft 132. The distal direction is indicated with an arrow D in FIGS. 10A-B. Arms 134 include a first arm 134A and a second arm 134B. In FIGS. 10A-B, a distal portion of each arm 134 can be seen extending through a passageway defined by staple 100. In the embodiment of FIGS. 10A-B, a trigger 160 is pivotably coupled to handle 148 of fixation tool 144. Trigger 160 is operatively coupled to staple push rod 130. In operation, staple push rod 130 will be advanced and/or retracted in an axial direction when trigger 160 is pivoted relative to handle 148.

Figure 11:
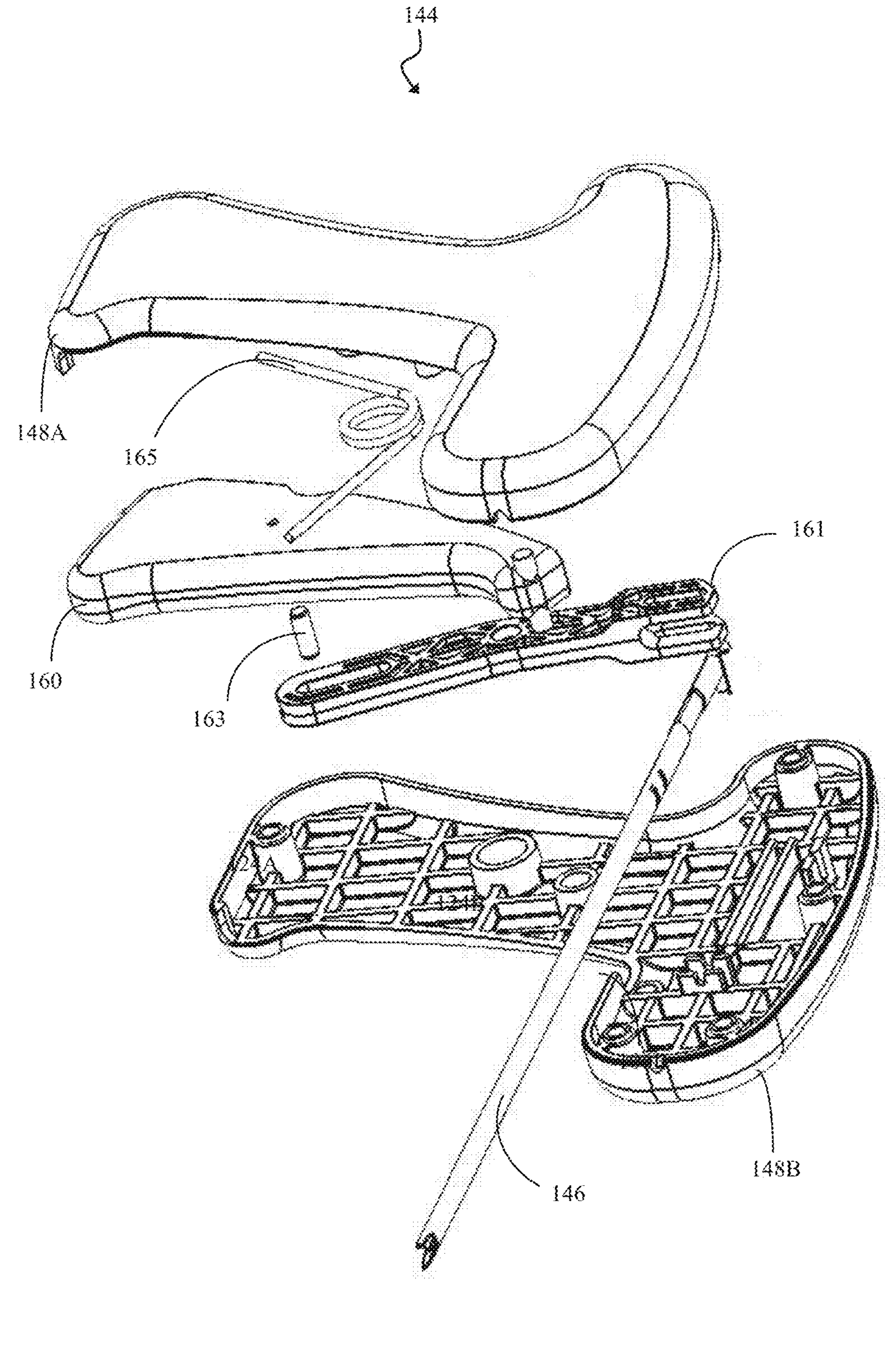
FIG. 11 is an exploded view illustrating some of the internal components of an exemplary fixation tool in accordance with the present disclosure.

FIG. 11 is an exploded view of fixation tool 144 showing internal components. In some examples, handle 148 may be formed from two separate halves, 148A, 148B. Inside handle 148, fixation tool 144 may comprise bias member 165, connecting member 163, and pivoting member 161. When assembled, connecting member 163 may connect trigger 160 to pivoting member 161. Additionally, bias member 165 may be positioned between and in contact with handle 148 and trigger 160 such that bias member 165 biases trigger 160 to a rest position. Fixation tool shaft 146 may be fixedly connected to handle 148, while staple push rod 130 (not shown in FIG. 11) is moveably received within fixation tool shaft 146. Pivoting member 161 may further be connected to staple push rod 130. When force is applied to trigger 160 in the opposite direction of the force applied by bias member 165, trigger 160 may move in an inward direction toward handle 148. This movement may cause a pivoting action in pivoting member 161. The pivoting action of pivoting member 161 may in turn cause staple push rod 130 to move within fixation tool shaft 146 toward the distal end of fixation tool shaft 146. In some examples, the distance staple push rod 130 moves is enough to move arms 134 past the distal end of fixation tool shaft 146.

Figure 12:
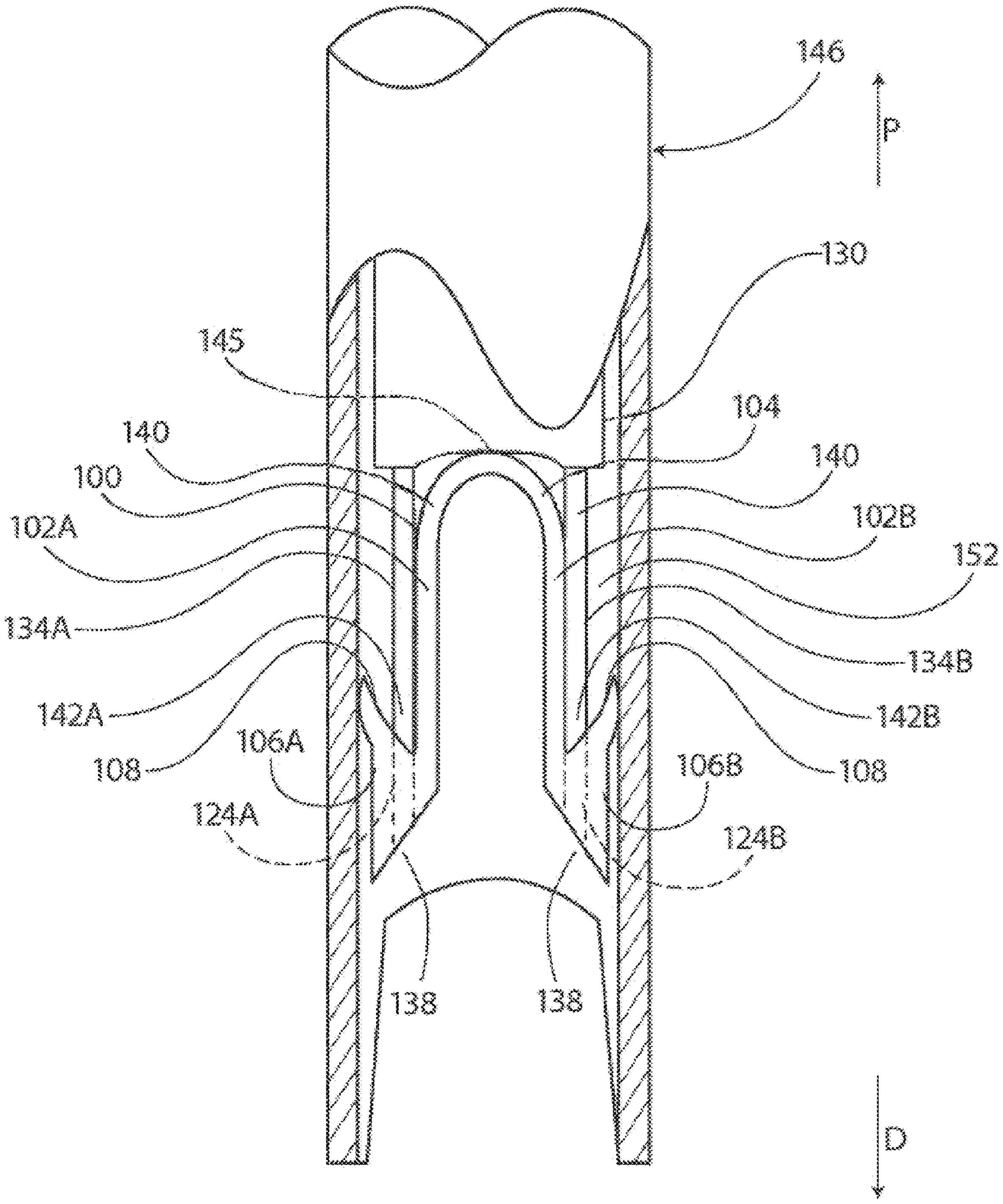
FIG. 12 is an enlarged partial cross-sectional view of a distal portion of the fixation tool shaft shown in FIGS. 10A-10B.

FIG. 12 is a further enlarged top view of a distal portion of fixation tool shaft 146 shown in the FIGS. 10A-B. For purposes of illustration, fixation tool shaft 146 is shown in partial cross-section in FIG. 12 so that staple 100 is visible residing in lumen 152. With reference to FIG. 12, it will be appreciated that staple 100 is disposed on a distal portion of staple push rod 130. As seen in FIG. 12, a distal portion 138 of first arm 134A and second arm 134B of staple push rod 130 is received within passageways 124A, 124B. In some examples, as in FIG. 12, no part of arms 134A, 134B extend distally beyond passageways 124A, 124B beyond the distal end of staple 100. However, in other examples, at least a portion of arms 134A, 134B may extend distally beyond passageways 124A, 124B. In FIG. 12, a first shoulder 142A of first arm 134A and a second shoulder 142B of second arm 134B are shown disposed proximate surfaces 108 of first fluke 106A and second fluke 106B.

As described previously, in some examples, as in the example of FIG. 12, first and second shoulders 142A, 142B may be disposed relatively more proximally on arms 134A, 134B such that shoulders 142A, 142B do not contact proximal surfaces 108A, 108B of flukes 106A, 106B. In such examples, pushing forces on staple push rod 130 may be transferred to staple 100 primarily by pushing of bridge 104 of staple 100 by bridge 145 of staple push rod 130. However, in other examples, shoulders 142A, 142B may be disposed relatively more distally on arms 134A, 134B such that shoulders 142A, 142B do contact proximal surfaces 108A, 108B of flukes 106A, 106B. In such examples, pushing forces on staple push rod 130 may be primarily transferred to staple 100 by shoulders 142A, 142B pushing on proximal surfaces 108 of flukes 106A, 106B. In these examples, a gap may be left between bridge 104 and bridge 145. In still additional examples, pushing forces on staple push rod 130 may be transferred to staple rod both by shoulders 142A, 142B pushing on proximal surfaces 108A, 108B of flukes

106A, 106B and by bridge 145 of staple push rod 130 pushing on bridge 104 of staple 100.

Figure 13A:
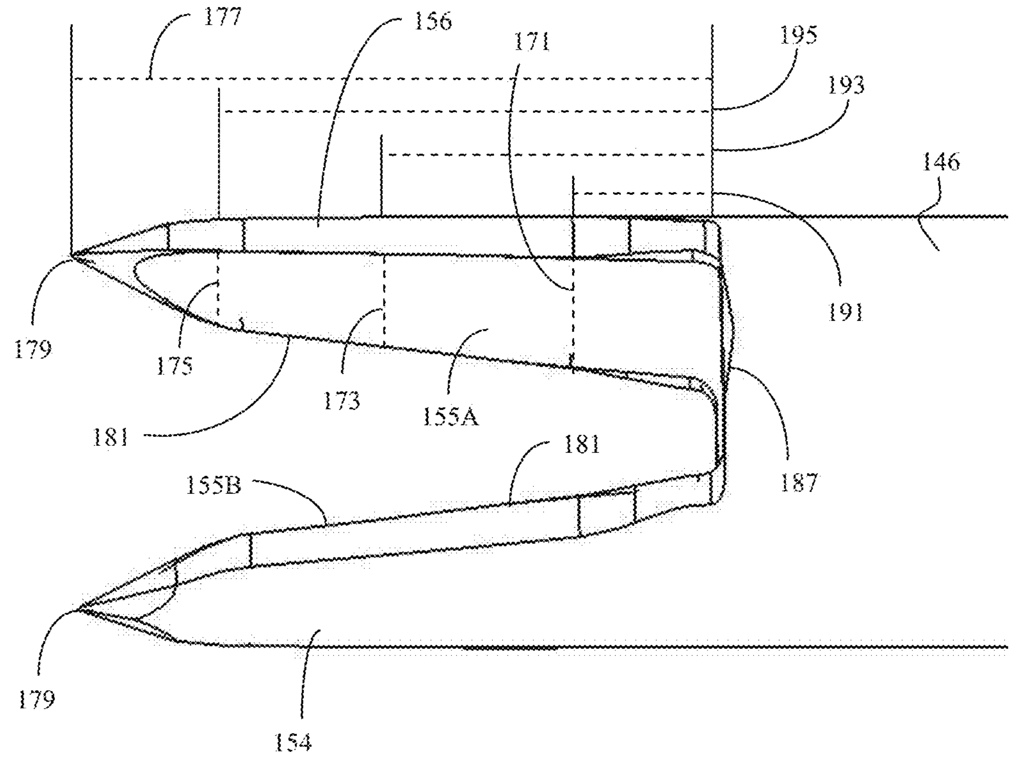
FIGS. 13A-B illustrate a perspective and a plan view of exemplary prongs of the fixation tool shaft shown in FIGS. 10A-10B and FIG. 12.
Figure 13B:
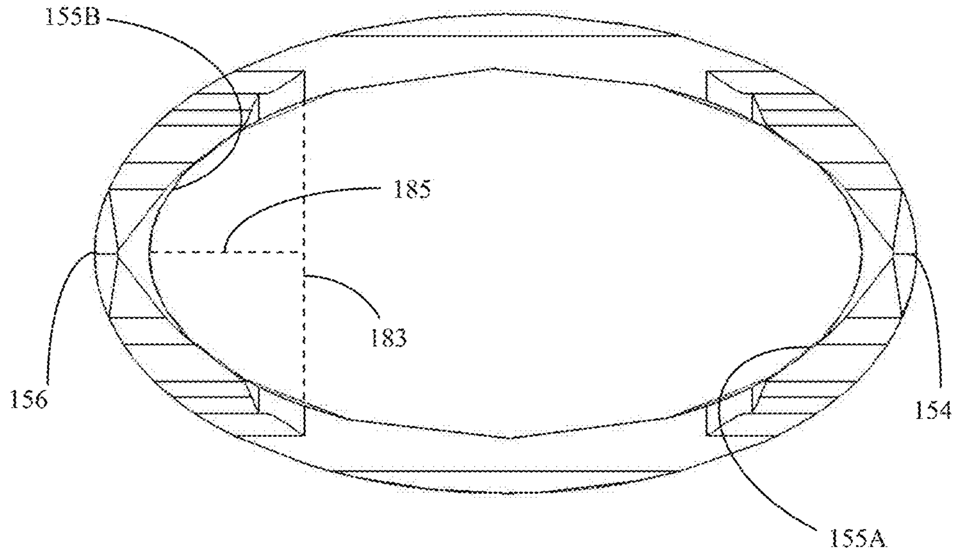

FIGS. 13A-B are plan views illustrating close-ups of prongs 154, 156 of fixation tool shaft 146. In some examples, prongs 154, 156 are used to cut patient tissue before deploying a fastener, such as staple 100. For instance, prongs 154, 156 may be positioned proximate target tissue. Force may be applied to prongs 154, 156 in the direction of the tissue. Prongs 154, 156 may cut the tissue as the prongs are advanced into the tissue. In such examples, tips 179 and edges 181 of prongs 154, 156 may be at least sharp enough to cut target tissue.

As seen in FIGS. 13A-B, prongs 154, 156 may be formed integrally from fixation tool shaft 146. In such examples, material may be removed from the distal end of fixation tool shaft 146 in order to create prongs 154, 156. In such examples, prongs 154, 156 may have curved inner faces 155A, 155B, and curved inner faces 155A, 155B may have a same curvature as the inner surface of fixation tool shaft 146. Accordingly, curved inner faces 155A, 155B may have a concave curvature. As depicted in FIG. 13B, in at least some examples, fixation tool shaft 146 and prongs 154, 156 may have a generally ovular curvature. However, in other examples, the curvature may be circular or there may be no curvature at all, for example if a cross section of fixation tool shaft 146 is rectangular or of a similar shape.

As seen in FIG. 13B, prong 156 may have a width 183 and a depth 185. The width may be measured across prong 156 from a first edge to a second edge. In some examples, width 183 may be between 0.05 inches (1.27 millimeters) and 0.07 inches (1.78 millimeters), and in some examples width 183 may be 0.058 inches (1.47 millimeters). Additionally, depth 185 may be between 0.02 (0.508 millimeters) inches and 0.04 inches (1.02 millimeters), and in some examples depth 185 may be 0.31 inches (7.87 millimeters). As seen in FIG. 13A, prong 156 may additionally have a length 177 that prong 156 extends distally beyond the main portion of fixation tool shaft 146, as measured from proximal base 187 of prongs 154, 156. Some example values for length 177 are between 0.15 inches (3.81 millimeters) and 0.35 inches (8.89 millimeters), and in some examples length 177 may be 0.222 inches (5.64 millimeters). Although, in other examples, prong 156 may not extend distally beyond fixation tool shaft 146 at all or only a small amount, for example between 0.01 inches (0.25 mm) and 0.1 inches (2.54 mm).

In some examples, prongs 154, 156 may taper distally toward tips 179. For instance, as depicted in FIG. 13A, widths 171, 173, and 175 of prong 156 may become smaller approaching tip 179. Some example values for width 171 are between 0.045 inches (1.14 millimeters) to 0.065 inches (1.65 millimeters), and in some examples width 171 may be 0.056 inches (1.42 millimeters). Width 171 may be measured a length 191 from proximal base 187, and some example values for length 191 are between 0.04 inches (1.02 millimeters) and 0.055 inches (1.40 millimeters). Example values for width 173 may be between 0.035 inches (0.889 millimeters) and 0.055 inches (1.40 millimeters), and in some examples width 173 may be 0.046 inches (1.17 millimeters). Width 173 may be measured a length 193 from proximal base 187, and some example values for length 193 are between 0.10 inches (2.54 millimeters) and 0.13 inches (3.30 millimeters). Example values for width 175 may be between 0.03 inches (0.762 millimeters) to 0.05 inches (1.27 millimeters), and in some examples width 175 may be 0.04 inches (1.02 millimeters). Width 175 may be measured a length 195 from proximal base 187, and some example values for length 195 are between 0.145 inches (3.68 millimeters) and 0.175 inches (4.45 millimeters).

In other examples, prongs 154, 156 may not be formed integrally from fixation tool shaft 146. In such examples, prongs 154, 156 may be attached to the distal end of fixation tool shaft 146 after being formed. Additionally, in such examples, prongs 154, 156 may not have curved inner faces 155A, 155B. Rather, prongs 154, 156 may take other shapes, such as spikes, rods, or even thin sheets. In such examples, the tips and edges of such shapes may still be sharp enough such that the tips and/or edges may cut through tissue.

In some examples, prongs 154, 156 may have dimensions that are related to the dimensions of staple 100. For instance, in some examples length 177 may correspond to a total length of staple 100, as measured from the tips of flukes 106A, 106B and bridge 104. In other examples, length 177 may correspond to between 50% and 120% of the length of staple 100, and in some examples length 177 may correspond to 90% the length of staple 100. In still other examples, length 177 may be chosen such that, when staple 100 is deployed into patient tissue, prongs 154, 156 extend into the tissue at least as much as, or a little more than, barbs 122A, 122B extend into the tissue. In such examples, having length 177 be selected such that prongs 154, 156 extend into patient tissue at least as far as barbs 122A, 122B may allow for easier deployment of staple 100 into tissue by pre-cutting the tissue to allow for insertion of the staple into the tissue.

Figure 14:
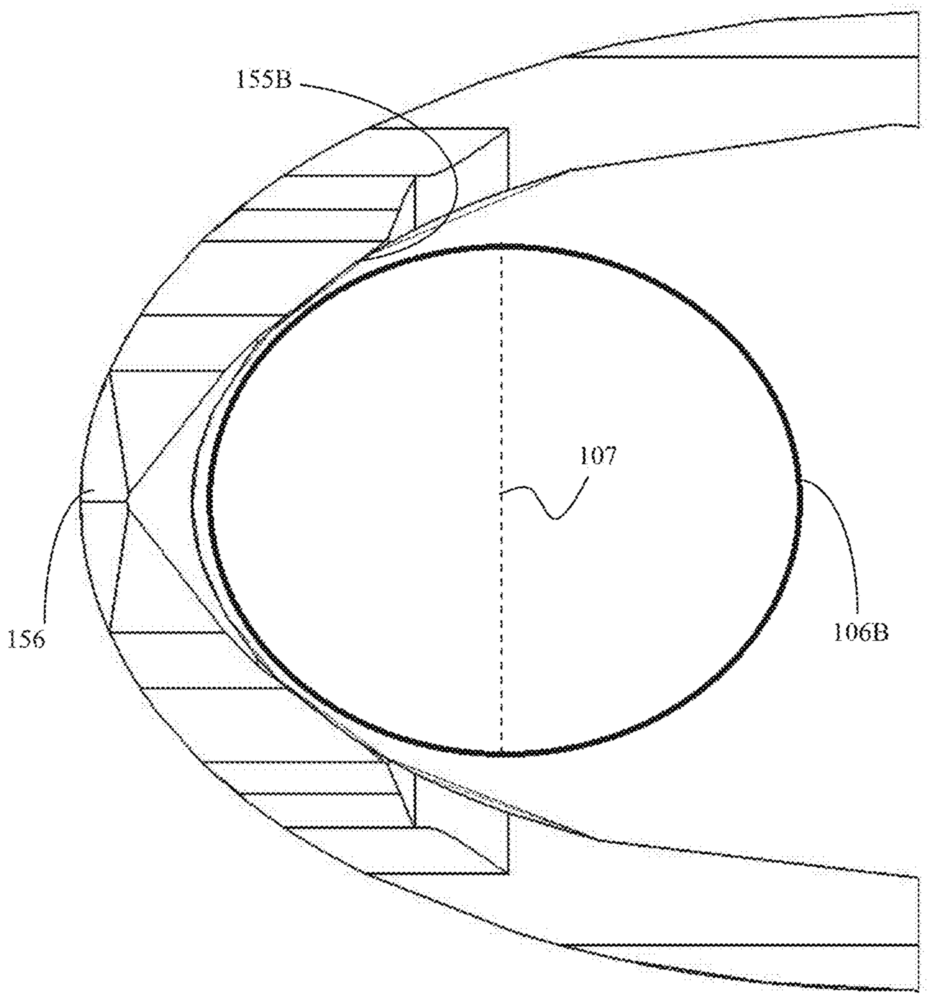
FIG. 14 is a plan view illustrating an example prong and a cross section of an example fastener or staple adjacent to the prong.

Widths 171, 173, and 175 may also have values that are related to dimensions of staple 100. For instance, flukes 106A, 106B of staple 100 may be modeled generally as cylinders, such as how fluke 106B is depicted in FIG. 14. In such examples, fluke 106B has a defined circumference and a diameter, as illustrated by height 107 in FIG. 14. Prong 156 may have a width 183 such that the arc-length defined by curved inner face 155B at proximal base 187 of prong 156 nearest matches the arc-length of fluke 106B along the same width. As one illustrative example, curved inner face 155B near proximal base 187 of prong 156 may define a half-circle and fluke 106B may be modeled as having a circular cross-section. In such examples, width 183 and height 107 may be equal. Accordingly, the arc-length of curved inner face 155B near proximal base 187 of prong 156 may be determined according to equation 1, where r is the radius of the half circle.

$$\text{Arc-length} = \pi * r \tag{1}$$

In the foregoing example, variable r would be half of width 183. In these examples, near proximal base 187 of prong 156, the arc-length of prong 156 would equal half of the circumference of fluke 106B.

Continuing the above example, as widths 171, 173, and 175 get progressively smaller towards tip 179, the arc-length defined by curved inner face 155B at those widths will be smaller than half the circumference of fluke 106B. As some examples, width 171 may be a value such that the arc-length defined by curved inner face 155B at width 171 is between 90% and 98% of half the circumference of fluke 106B. Width 173 may be a value such that the arc-length defined by curved inner face 155B at width 173 is between 70% and 85% of half the circumference of fluke 106B. Additionally, width 175 may be a value such that the arc-length defined by curved inner face 155B at width 175 is between 60% and 70% of half the circumference of fluke 106B.

In other examples, widths 183, 171, 173, and 175 may have proportions relative to height 107 of fluke 106B. For instance, width 183 of prong 156 may be between 90% and 110% of height 107 of fluke 106. Width 171 may be between 85% and 95% of height 107. Width 173 may be between 70% and 85% of height 107, and width 175 may be between 60% and 75% of height 107.

Although the above example assumed that curved inner surface 155B of prong 156 defined a half circle and that fluke 106B had a circular cross-section, in other examples prong 156 and fluke 106B may differ. For instance, in some examples, curved inner surface 155B of prong 156 may be ovular in shape and fluke 106B may have ovular cross-section. In still other examples, curved inner surface 155B of prong 156 may be ovular in shape while fluke 106B generally has a circular cross-section. In these and other examples, the relative dimensions of arc-lengths of prong 156 at widths 171, 173, and 175 of prong 156 to half of the circumference of fluke 106B may differ.

Having widths 171, 173, and 175 with values such that curved inner face 155B has arc-lengths at those widths smaller than half the circumference of fluke 106B may help to retain staple 100 once deployed in tissue. For instance, when fluke 106B is deployed into the tissue cut by prong 156, the cut tissue will need to stretch around fluke 106B, as the cut material would not be wide enough to accommodate the width of fluke 106B. When prong 156 is subsequently removed, the stretched tissue may attempt collapse back together which may bring tissue in behind barb 122B of fluke 106B. By stretching the tissue and having the tissue collapse back around fluke 106B, the tissue may be more likely to catch on barb 122B, thereby securing staple 100 in the tissue. Although the above examples were described respect to prong 156, prong 154 may be formed in a similar fashion and/or have similar dimensions.

Figure 15A:
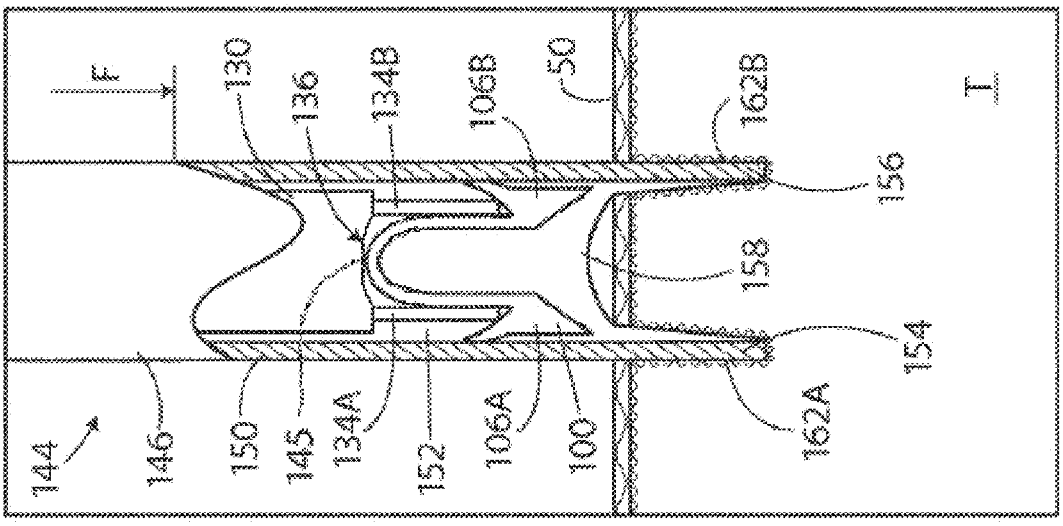
FIGS. 15A-15C are a sequence of plan views illustrating an exemplary method and apparatus in accordance with the present disclosure.
Figure 15B:
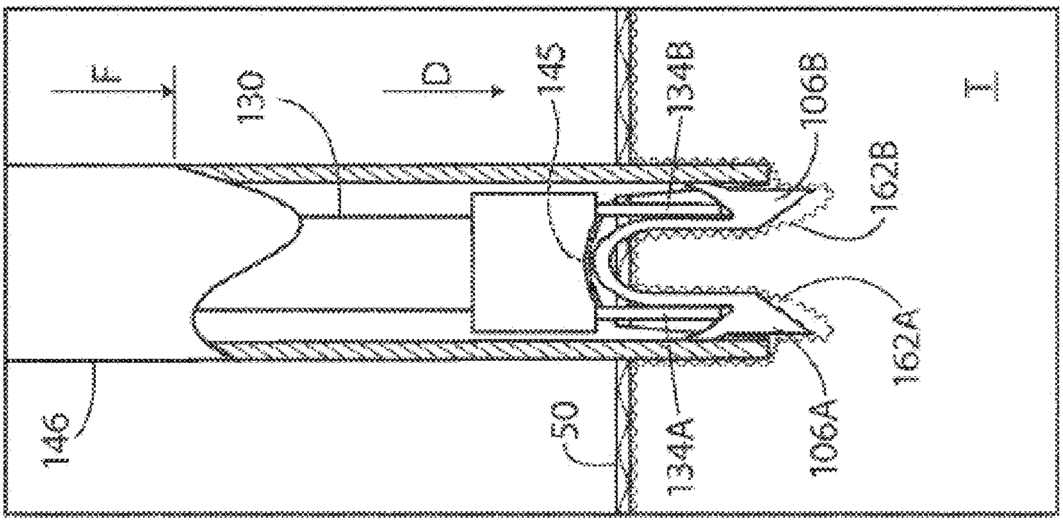
Figure 15C:
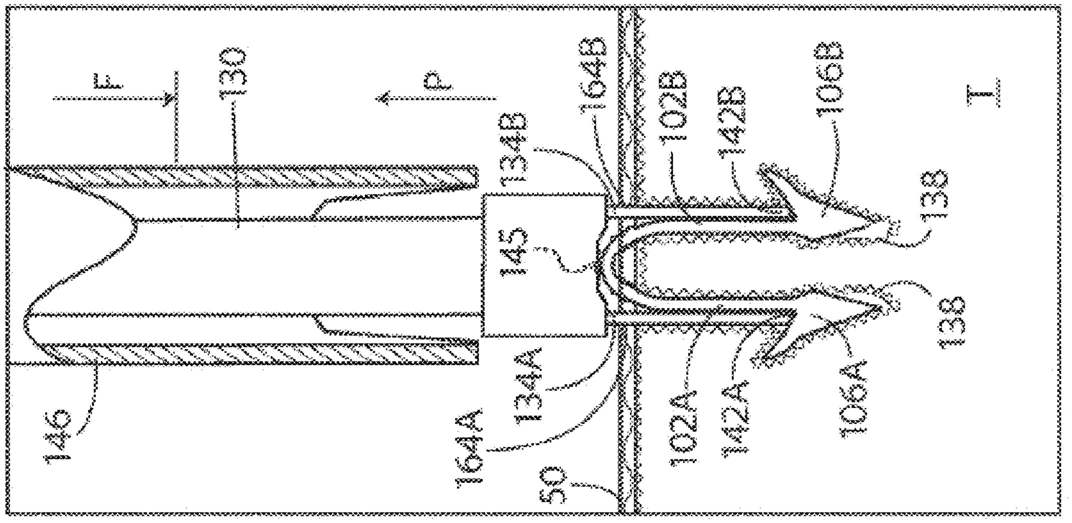

FIGS. 15A-15C are a sequence of plan views illustrating an exemplary method in accordance with the present disclosure. The exemplary method illustrated in FIGS. 15A-C may be used, for example, to fix a tendon repair implant 50 to a target tissue T using a staple 100.

In the examples of FIGS. 15A-C, fixation tool 144 includes a fixation tool shaft 146 comprising a wall 150 defining a lumen 152. With reference to FIGS. 15A-C, it will be appreciated that fixation tool shaft 146 includes a first prong 154 and a second prong 156 that extend distally beyond a distal end 158 of lumen 152. In the example of FIG. 15A, first prong 154 and second prong 156 have been urged into tissue T to form first pilot hole 162A and second pilot hole 162B. In FIG. 15A a distally directed force F applied to fixation tool shaft 146 is illustrated using an arrow. Force F may be produced, for example, by pushing on a handle that is fixed to a proximal portion of fixation tool shaft 146. It will be appreciated that in some examples, such as the example depicted in FIG. 6, one of the first and second pilot holes may be formed through the sheet-like implant and the target tissue, and the other pilot hole may be formed directly in the target tissue without passing through the sheet-like implant. In such examples, staples may straddle the perimeter edge of the sheet-like implant (as shown in FIG. 6). However, in other examples, both pilot holes may be formed through the sheet-like implant and the target tissue.

The staples may be applied adjacent to the perimeter, and/or be applied to a central region of the sheet-like implant. In some examples, the staples may be used to attach the implant to soft tissue and/or to bone. In FIG. 15A, a staple 100 can be seen residing in lumen 152 of fixation tool shaft 146. For purposes of illustration, fixation tool shaft 146 is shown in partial cross-section in FIG. 15A so that staple 100 is visible residing in lumen 152. With reference to FIGS. 15A-C, it will be appreciated that staple 100 is carried by a fork 136 comprising a first arm 134A and a second arm 134B. In FIG. 15A, a distal portion of first arm 134A of staple push rod 130 can be seen extending into a first passageway defined by first arm 106A. A distal portion of second arm 134B of staple push rod 130 can be seen extending into a second passageway defined by second fluke 106B of staple 100.

In some examples, each arm is positioned relative to a prong along an inner surface of fixation tool shaft 146 so that the arms advance into the pilot holes when the arms are moved in a distal direction. Staple push rod 130 is moveably disposed within lumen 152 defined by fixation tool shaft 146. Fixation tool 144 includes a mechanism that is capable of creating relative axial motion between staple push rod 130 and fixation tool shaft 146 so that staple push rod 130 moves along fixation tool shaft 146.

At FIG. 15B, relative motion has been created between staple push rod 130 and fixation tool shaft 146 while distally directed force F has been continuously applied to fixation tool shaft 146. By comparing FIG. 15B and FIG. 15A, it will be appreciated that first arm 134A and second arm 134B have been advanced in a distal direction D. With reference to FIGS. 15A-B, it will also be appreciated that first arm 134A and second arm 134B have advanced into first pilot hole 162A and second pilot hole 162B, respectively. In FIG. 15B, first fluke 106A is shown residing in first pilot hole 162, and second fluke 106B is residing in second pilot hole 162.

At FIG. 15C, additional relative motion has been created between staple push rod 130 and fixation tool shaft 146 while distally directed force F has been continuously applied to fixation tool shaft 146. By comparing FIG. 15C and FIG. 15B, it will be appreciated that the relative motion between staple push rod 130 and fixation tool shaft 146 has moved fixation tool shaft 146 in a proximal direction P.

By comparing FIG. 15C and FIG. 15B, it will also be appreciated that first arm 102A of staple 100 has been bent and first fluke 106A has been rotated to a toggled position. In the exemplary embodiment of FIG. 15C, force applied to first fluke 106A by bridge 145, and through arm 102A, has caused first fluke 106A to rotate. With continuing reference to FIG. 15C and FIG. 15B, it will also be appreciated that second arm 102B of staple 100 has been bent and second fluke 106B has been rotated to a toggled position. Again, the force applied to second fluke 106B by bridge 145, and through arm 102B, has caused second fluke 106B to rotate.

With reference to FIG. 15C, it will be appreciated that a first through hole 164A and a second through hole 164B have been formed in tendon repair implant 50. In the embodiment of FIGS. 15A-C, first through hole 164A and a second through hole 164B were created by urging first prong 154 and second prong 156 of fixation tool shaft 146 through tendon repair implant 50. Once the staple has been deployed into tissue as in FIG. 15, the user may then release trigger 160, thereby drawing staple push rod 130 out of the tissue. In such examples, the force of the tissue holding the staple within the tissue may be greater than the friction force between the detents of arms 134A, 134B of staple push rod 130 and the inner surface of the passageways of the staple, which allows arms 134A, 134B to be withdrawn without also withdrawing the staple from the tissue.

In some examples, a staple or fastener, such as staple 100, may be preloaded for use on arms 134 inside fixation tool shaft 146. However, in some instances, a user may deploy multiple fasteners to fix tendon repair implant 50 to the tendon or bone. In such examples, a device such as staple loader 500, as illustrated in FIG. 16, may be useful in assisting a user to load and deploy multiple staples to fix tendon repair implant 50 to the tendon or bone in a time efficient manner.

Figure 16:
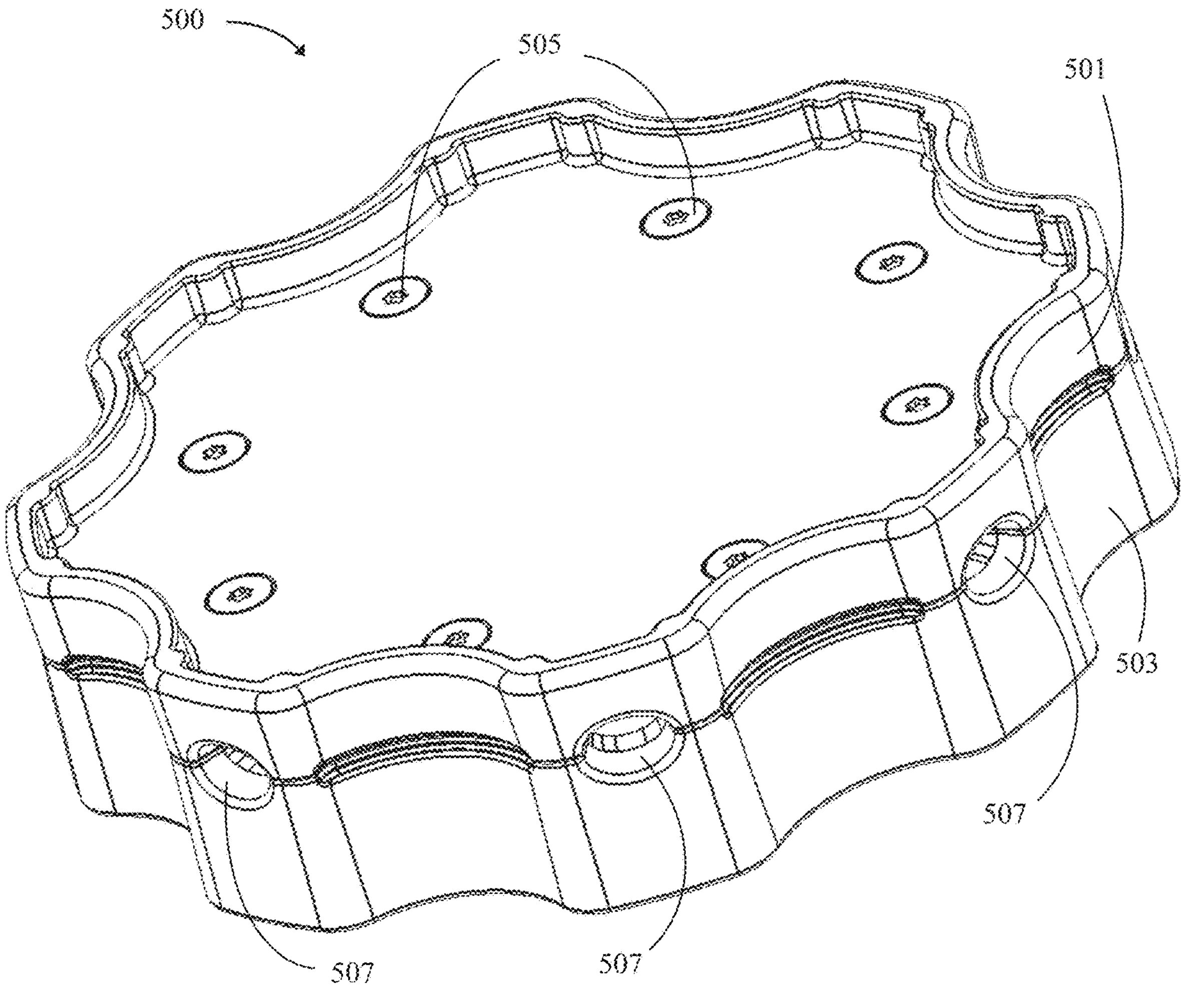
FIG. 16 is a perspective view of an example staple loader in accordance with the present disclosure.

FIG. 16 illustrates an example of staple loader 500. In some examples, staple loader 500 may comprise first half 501 and second half 503. In such examples, staples may be loaded onto one of halves 501, 503 and halves 501, 503 may then be secured together to hold the staples in place. Halves 501, 503 may be secured together through any suitable means. In at least some examples, halves 501, 503 may be secured together in a manner such that halves 501, 503 may be detachable to facilitate loading additional staples. In the example of FIG. 16, halves 501, 503 are secured together using screws 505, however in other examples other types of fasteners may be used.

FIG. 16 also depicts loading channels 507. Loading channels 507 are holes in staple loader 500 that have been sized appropriately to receive the distal end of fixation tool shaft 146. In order to load a staple, a user may insert the distal end of fixation tool shaft 146 into one of loading channels 507 which contains a staple. Once received in a loading channel 507, the user may depress trigger 160 to extend a portion of staple push rod 130, including arms 134, beyond the distal end of fixation tool shaft 146. The inside of staple loader 500, as illustrated in further figures, is configured such that when arms 134 extend beyond the distal end of fixation tool shaft 146, arms 134 are received into passageways of the staple. The friction fit between detents 137A, 137B and the passageways of the staple secure the staple to arms 134. When the user releases pressure on trigger 160, staple push rod 130 moves proximally, pulling arms 134 and the staple into lumen 152 of fixation tool shaft 146.

Figure 17A:
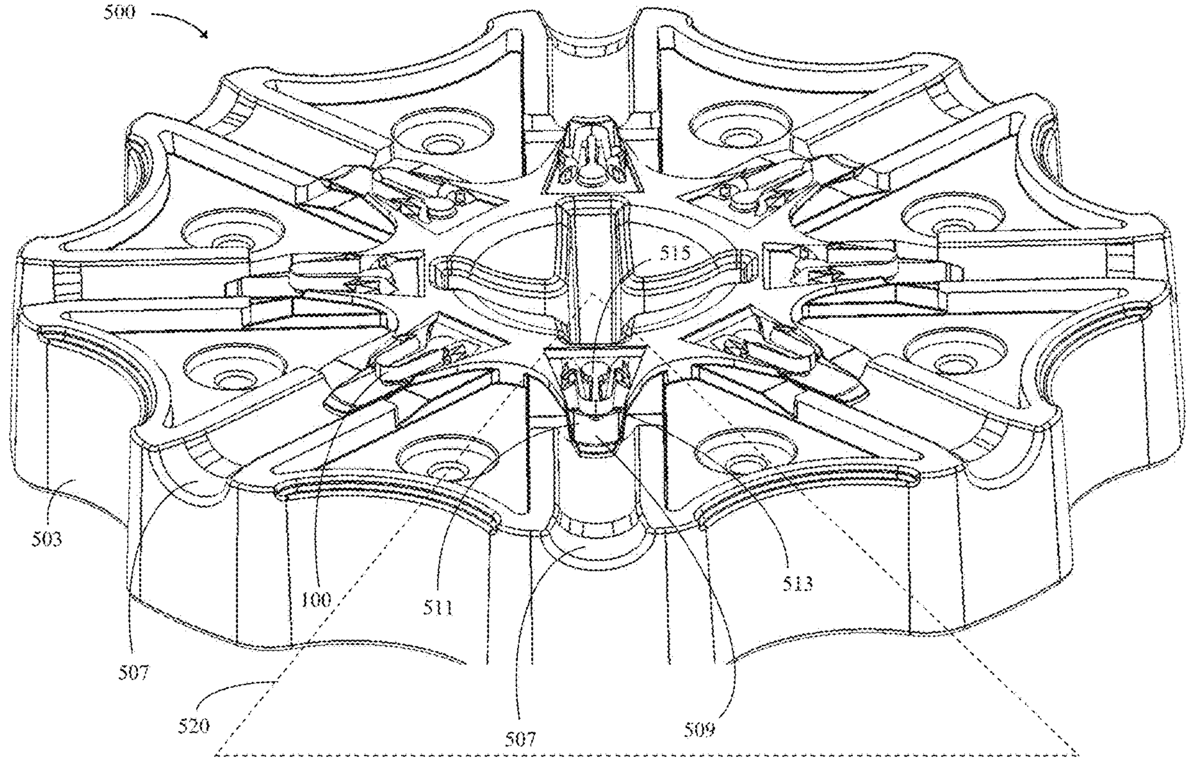
FIGS. 17A-17B are views illustrating various internal features of the exemplary staple loader shown in FIG. 16.

FIG. 17A more clearly depicts the internals of staple loader 500. More specifically, FIG. 17A shows half 503 of staple loader 500. The internals of FIG. 17A include staples 100, narrow channel 509 created by angled sides 511, 513, and staple holder 515. When loaded into staple loader 500, staples 100 may be disposed around staple holders 515. In some examples, staple holders 515 may have a circular portion and a straight portion jutting off of the circular portion. The end of the straight portion may abut staple 100 proximate bridge 104. When staple 100 is loaded inside staple loader 500, staple 100 and staple holder 515 may be arranged such that staple 100 remains in place by pressing against staple holder 515 when a force is applied to staple 100 in a direction toward the center of staple loader 500. The circular portion of staple holder 515 may prevent arms 102A, 102B and/or flukes 106A, 106B from compressing inward toward one another.

Figure 17B:
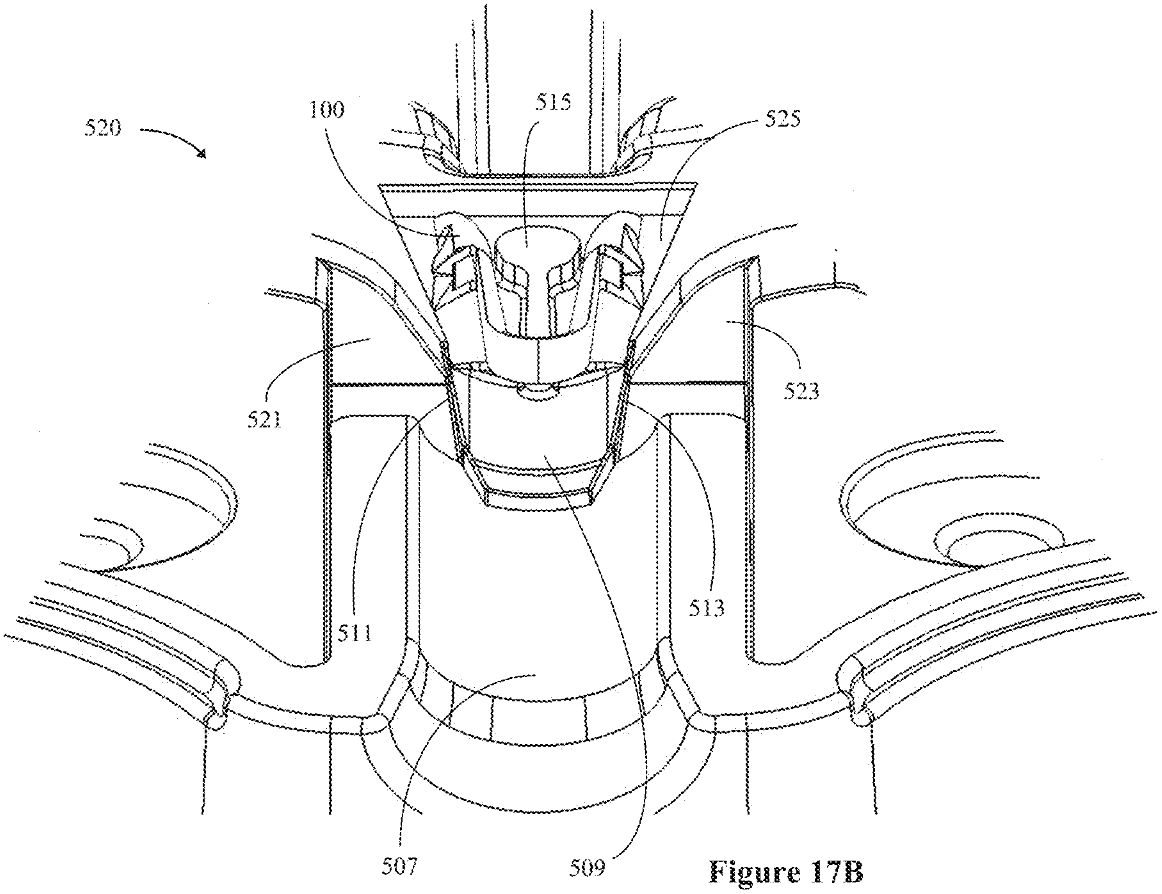

Region 520 of FIG. 17A can be seen in close-up in FIG. 17B. FIG. 17B more clearly depicts cavity 525 in which staple 100 resides and an example structure of staple holder 515. Additionally, FIG. 17B more clearly depicts angled sides 511, 513. Generally, angled sides 511, 513 may angle towards each other as angled sides 511, 513 extend away from cavity 525. In some examples, angled sides 511, 513 may extend at a constant angle away from cavity 525 along their entire length. However, in other examples, as depicted in the example of FIG. 17B, angled sides 511, 513 may have a first region and a second region, where the first region is canted at a first angle, and the second region is canted at a second angle that is different than the first angle. In general, angled sides 511, 513 operate to create an opening at the end of narrow channel 509. The distance across the opening of narrow channel 509 created by angled sides 511, 513 is generally less than the lateral distance between the two outward edges of flukes 106A, 106B of staple 100.

When fixation tool shaft 146 is inserted into loading channel 507 in FIG. 17B, prongs 154, 156 may extend into prong cavities 521, 523. Prong cavities 521, 523 and angled sides 511, 513 may be sized relative to prongs 154, 156 such that when prongs 154, 156 reside within prong cavities 521, 523, the opening of narrow channel 509 extends at least partially within lumen 152 of fixation tool shaft 146. When received within loading channel 507 in this manner, as described above, a user may depress trigger 160 to extend arms 134. Arms 134 may extend through narrow channel 509 and into cavity 525. When arms 134 are extended, they may extend into the passageways of the flukes of staple 100. The friction fit between detents 137A, 137B secures staple 100 to arms 134. As the user releases pressure on trigger 160, arms 134, with staple 100 secured thereto, may be drawn back within lumen 152 of fixation tool shaft 146. As staple 100 is drawn through the opening of narrow channel 509, arms 102A, 102B and/or flukes 106A, 106B may be compressed inward. This compression allows for staple 100 to advance into lumen 152 of fixation tool shaft 146 without barbs 122A, 122B catching on prongs 154, 156 or the edges of fixation tool shaft 146. Once arms 134 have been fully retracted within lumen 152 of fixation tool shaft 146, the fixation tool containing fixation tool shaft 146 is ready to deploy staple 100 to the target site.

Although depicted in FIGS. 16 and 17A-B as a generally circular or octagon device, in other examples staple loader 500 may comprise any other suitable shape, such as a square or hexagon. Additionally, in the depicted examples, staple loader 500 was shown with a capacity of eight staples. In other examples, staple loader 500 may have room for any suitable number of staples. In at least some examples, staple loader 500 may have a capacity for a number of staples that is slightly more than a user may regularly use during a procedure for affixing implant 50 to tendon or bone. For example, if securing implant 50 to the tendon or bone generally requires eight staples, staple loader 500 may have capacity for ten staples. In still additional examples, staple loader 500 may be configured to hold multiple different types of staples. For example, as described with respect to previous figures, in some examples implant 50 may be secured to both the tendon and to bone. In some of these examples, different fasteners or staples may be used depending on whether the fastener will be deployed within the tendon or within the bone. In these examples, staple loader 500 may be configured to hold one or more of staples that are configured to be deployed into tendon and one or more staples that are configured to be deployed into bone. In such examples, cavities 525 and staple holder 515 may be designed slightly differently to accommodate for differences in the sizes and shapes of the staples that are configured to be deployed into tendon and the staples that are configured to be deployed into bone.

Accordingly, it should be generally understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed:

1. A fastener delivery system comprising:

a fastener push rod having a shaft, a first arm, and a second arm, the first and second arms extending distally from a distal end of the shaft, wherein the first arm and the second arm each include an enlarged portion proximate a distal end thereof, and a fastener comprising:

a first arm;

a second arm;

a bridge extending from a proximal end of first arm to proximal end of the second arm;

a first fluke extending distally from a distal end of the first arm, the first fluke extending from a proximal end and a distal end and defining a first passageway extending therethrough;

a second fluke extending distally from a distal end of the second arm, the second fluke extending from a proximal end and a distal end and defining a second passageway extending therethrough;

wherein the first and second passageways are configured to receive the first and second arms of the fastener push rod therein; and when the first and second arms of the fastener push rod are within the first and second passageways, the enlarged portion of each of the first and second arms of the fastener push rod are distal to the proximal end of each of the first and second flukes.

2. The fastener delivery system of claim 1, wherein the enlarged portion of the first and second arms of the fastener push rod has at least one dimension greater at least one dimension of the first and second passageways.

3. The fastener delivery system of claim 1, wherein the proximal end of each of the first and second flukes each include a proximal end surface.

4. The fastener delivery system of claim 3, wherein the proximal end surface of each of the first and second flukes each extend at an outward angle away from the distal end of each of the first and second arms of the fastener.

5. The fastener delivery system of claim 1, wherein the first and second arms of the fastener push rod are formed as one or more separate pieces from the shaft.

6. The fastener delivery system of claim 1, wherein the fastener is a single-piece staple.

7. The fastener delivery system of claim 1, wherein the first fluke is eccentrically mounted to the first arm of the fastener and the second fluke is eccentrically mounted to the second arm of the fastener.

8. The fastener delivery system of claim 1, further comprising a fixation tool having a shaft extending to a distal end and defining a lumen.

9. The fastener delivery system of claim 8, wherein the fastener push rod is movably disposed within the lumen of the shaft of the fixation tool.

10. The fastener delivery system of claim 1, wherein the first and second arms of the fastener push rod are secured to a connection member.

11. The fastener delivery system of claim 10, wherein the connection member is coupled to the distal end of the shaft.

* * * * *